United States Patent
Olek

(10) Patent No.: US 12,006,546 B2
(45) Date of Patent: Jun. 11, 2024

(54) METHOD FOR EPIGENETIC IMMUNE CELL DETECTION AND COUNTING IN HUMAN BLOOD SAMPLES

(71) Applicant: Precision for Medicine GmbH, Berlin (DE)

(72) Inventor: Sven Olek, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 576 days.

(21) Appl. No.: 17/256,390

(22) PCT Filed: Jul. 3, 2019

(86) PCT No.: PCT/EP2019/067876
§ 371 (c)(1),
(2) Date: Dec. 28, 2020

(87) PCT Pub. No.: WO2020/007928
PCT Pub. Date: Jan. 9, 2020

(65) Prior Publication Data
US 2022/0090196 A1 Mar. 24, 2022

(30) Foreign Application Priority Data
Jul. 5, 2018 (DE) .......... 102018116353.3

(51) Int. Cl.
*C12Q 1/6881* (2018.01)
*C12Q 1/6883* (2018.01)

(52) U.S. Cl.
CPC ......... *C12Q 1/6881* (2013.01); *C12Q 1/6883* (2013.01); *C12Q 2600/154* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 9,926,599 B2 * | 3/2018 | Olek .................... | C12Q 1/6881 |
| 11,319,581 B2 * | 5/2022 | Olek .................... | C12Q 1/6881 |
| 2012/0107810 A1 | 5/2012 | Olek et al. | |
| 2015/0004602 A1 * | 1/2015 | Olek .................... | C12Q 1/6881 |
| | | | 536/23.1 |
| 2017/0233807 A1 | 8/2017 | Olek et al. | |

FOREIGN PATENT DOCUMENTS

| | | | |
|---|---|---|---|
| EP | 2199411 A1 | 12/2008 | |
| WO | 2012098215 A1 | 7/2012 | |
| WO | 2013135454 A1 | 9/2013 | |
| WO | 2014080017 A1 | 5/2014 | |
| WO | 2014170497 A2 | 10/2014 | |
| WO | 2017050882 A1 | 3/2017 | |
| WO | 2017050916 A1 | 3/2017 | |

OTHER PUBLICATIONS

Ahern, H. The Scientist. Jul. 1995. 9(15): 20-25 (Year: 1995).*
Ehrlich et al. Oncogene 2002. 21: 5400-5413 (Year: 2002).*
Yu et al., Relationship between CD4 count and CD4% in HIV-infected people, Int. J. Epidemiol. vol. 26, No. 6, 1367-1372 (1997).
Baron et al., Epigenetic immune cell counting in human blood samples for immunodiagnostics, Science Translational Medicine, 10, (2018), 1-11.
Accomando et al., Quantitative reconstruction of leukocyte subsets using DNA methylation, Genome Biol. 15, (2014).
Adan et al., Flow cytometry: basic principles and applicatoins, Critical Reviews in Biotechnology, 8551, 1-14 (2016).
Barbaro et al., Newborn Screening for Severe Primary Immunodeficiency Diseases in Sweden—a 2-Year Pilot TREC and KREC Screening Study, J. Clin. Immunol. 37, 51-60 (2017).
Baron et al., DNA demethylation in the human FOXP3 locus discriminates regulatory T cells from activated FOXP3+ conventional T cells, Eur. J. Immunol. 37, 2378-2389 (2007).
Barzaghi et al., Demethylation analysis of the FOXP3 locus shows quantitative defects of regulatory T cells in IPEX-like syndrome, J.Autoimmun. 38, 49-58 (2012).
Bin Dhuban et al., The immunological and genetic basis of immune dysregulation, polyendocrinopathy, enteropathy, X-linked syndromeCurr. Opin. Allergy Clin. Immunol. 15, 525-532 (2015).
Boldt et al., Eight-color immunophenotyping of T-, B-, and NK-cell subpopulations for characterization of chronic immunodeficiencies, Cytom. Part B—Clin. Cytom. 86, 191-206 (2014).
Borte et al., Neonatal screening for severe primary immunodeficiency diseases using high-throuput triplex real-time PCR, Blood 119, 2552-2555 (2012).
Brown et al, Neonatal diagnosis of severe combined immunodeficiency leads to significantly improved survival outcome: The case for newborn screening, Blood 117, 3243-3246 (2011).
Chaisomchit et al., Stability of genomic DNA in dried blood spots stored on filter paper, Southeast Asian J. Trop. Med. Public Health 36, 270-273 (2005).
Chen et al., Differential reactivity of the rat S100A4(p9Ka) gene to sodium bisulfite is associated with differential levels of the S100A4 (p9Ka) mRNA in rat mammary epithelial cells, J. Biol. Chem. 274, 2483-2491 (1999).
De Jonge et al., Evidence Based Selection of Housekeeping Genes, PLoS One 2, e898 (2007).
Ghani et al., Segmental duplications in genome-wide significant loci and housekeeping genes; warning for GAPDH and ACTB, Neurobiol. Aging 34 (2013), doi:10.1016/j.neurobiolaging.2012.11.006.
Giavarina et al., Understanding Bland Altman analysis, Biochem. Medica 25, 141-151 (2015).

(Continued)

*Primary Examiner* — Carla J Myers
(74) *Attorney, Agent, or Firm* — BakerHostetler

(57) ABSTRACT

The present invention relates to improved methods for epigenetic blood and immune cell detection and counting, and respective uses and kits.

17 Claims, 14 Drawing Sheets
Specification includes a Sequence Listing.

(56) References Cited

OTHER PUBLICATIONS

Harrison et al., Cytosines adjacent to methylated CpG sites can be partially resistant to conversion in genomic bisulfite sequencing leading to methylation artifactsAnal. Biochem. 264, 129-132 (1998).

Hauck et al., Pathogenic mechanisms and clinical implications of congenital neutropenia syndromesCurr. Opin. Allergy Clin. Immunol. 13, 596-606 (2013).

Herzenberg et al., Interpreting flow cytometry data: A Guide for the perplexed, Nat. Immunol., 7, 681-685 (2006).

Hollegaard et al., DNA methylome profiling using neonatal dried blood spot samples: A proof-of-principle study, Mol. Genet. Metab. 108, 225-231 (2013).

Hollegaard et al., Genotyping whole-genome-amplified DNA from 3-to 25-year-old neonatal dried blood spot samples with reference to fresh genomic DNA, Electrophoresis 30, 2532-2535 (2009).

Holmes et al., Performance evaluation of kits for bisulfite-conversion of DNA from tissues, cell lines, FFPE tissues, aspirates, lavages, effusions, plasma, serum, and urine, PLoS One 9 (2014), doi: 10.1371/journal.pone.0093933.

Houseman et al., DNA methylation arrays as surrogate measures of cell mixture distribution, BMC Bioinformatics 13 (2012).

J. van der Spek et al., TREC Based Newborn Screening for Severe Combination Immunodeficiency Disease: A Systematic Review, J. Clin. Immunol 35, 416-430 (2015).

King et al., Newborn Screening for Primary Immunodeficiency Diseases: The Past, the Present and the Future, Int. J. Neonatal Screen, 3, 19 (2017).

Kleen et al., Quantitative real-time PCR assisted cell counting (qPACC) for epigenetic-based immune cell quantification in blood and tisse, J.Immunother. Cancer 3 (2015).

Krzystek-Korpacka et al., Expression stability of common housekeeping genes is differently affected by bowel inflammation and cancer: Implications for finding suitable normalizers for inflammatory bowel disease studies, Inflamm. Bowel Dis. 20, 1147-1156 (2014).

Kung et al., Monoclonal antibodies defining distinctive h uman T cell surface antigens., Science (80-), 206, 347-349 (1979).

Kverneland et al., Age and gender leucocytes variances and reference svalues generated using the standarized One-Study protocol, Cytom. Part A 89, 543-564 (2016).

Lee et al., Fit-for-Purpose Method Development and Validation for Successful Biomarker Measurement, Pharmaceutical Research, (2006), vol. 23, pp. 312-328.

Lewin et al., Quantitative DNA methylation analysis based on four-dye trace data from direct sequencing of PCR amplificates, Bioinformatics 20, 3005-3012 (2004).

Maecker et al., A model for harmonizing flow cytometry in clinical trial Nat. Immunol. 11, 975-978 (2010).

Maecker et al., Standardizing immunophenotyping for the Human Immunology Project, Nat. Rev. Immunol. 12, 191-200 (2012).

Miziorko et al., Enzymes of the mevalonate pathway of isoprenoid biosynthesisArch. Biochem. Biophys. 505, 131-143 (2011).

Mizuguchi et al., LRP5, low-density-lipoprotein-receptor-related protein 5, is a determinant for bone mineral density, J. Hum. Genet. 49, 80-86 (2004).

Moore et al., CD4 percentage is an independent predictor of survival in patients starting antiretroviral therapy with absolute CD4 cell counts between 200 and 350 cells/microL, HIV Med 7, 383-388 (2006).

Nebe et al., Messunsicherheit und Qualitatssicherung im Bereich der Immunphanotypisierung der Lymphozytensubpopulationen im peripheren Blut LaboratoriumsMedizin 37, 233-250 (2013).

Reinherz et al., Regulation of the Immune Response—Inducer and Suppressor T-Lymphocyte Subsets in Human Beings, N.Engl. J. Med. 303, 370-373 (1980).

Rapko et al., DNA methylation analysis as novel tool for quality control in regenerative medicine, Tissue Eng. 13, 2271-2280 (2007).

Read et al., Recovery efficiencies of nucleic acid extraction kits as measured by quantitative LightCyclerTM PCR, J. Clin. Pathol.—Mol. Pathol. 54, 86-90 (2001).

Redl et al., Human tear lipocalinBiochim. Biophys. Acta—Protein Struct. Mol. Enzymol. 1482, 241-248 (2000).

Rodriguez et al., A microchip CD4 counting method for HIV monitoring in resource-poor settings, PLoS Med. vol. 2, 0663-0672 (2005).

Ryom et al., Essentials from the 2015 European AIDS Clinical Society (EACS) guidelines for the treatment of adult HIV-positive persons, HIV Med. 17, 83-88 (2016).

Schmidt et al., Autoimmunity and primary immunodeficiency: Two sides of the same coin? Nature Reviews—Rheumatology, 14, 7-18 (2018).

Sehouli et al., Epigenetic quantification of tumor-infiltrating T-lymphocytes, Epigenetics 6, 236-246 (2011).

Sottini et al., Simultaneous quantification of recent thymic T-cell and bone marrow B-cell emigrants in patients with primary immunodeficiency undergone to stem cell transplantation, Clin. Immunol. 136, 217-227 (2010).

Stajich et al., An Introduction to BioPerl., Methods Mol. Biol. 406, 535-548 (2007).

Tsikas et al., A proposal for comparing methods of quantitative analysis of endogenous compounds in biological systems by using the relative lower limit of quantification (rLLOQ), J. Chromatogr. B Anal. Technol. Biomed. Life Sci. 877, 2244-2251 (2009).

Warnecke et al., Detection and measurement of PCR bias in quantitative methylation analysis of bisulphite-treated DNA, Nucleic Acids Res. 25, 4422-4426 (1997).

Whitby et al., Current laboratory practices in flow cytometry for the enumeration of CD4+T-lymphocyte subsets, Cytom. Part B—Clin. Cytom., 88, 305-311 (2015).

Wieczorek et al., Quantitative DNA methylation analysis of FOXP3 as a new method for counting regulatory T cells in peripheral blood and solid tissue, Cancer Res. 69, 599-608 (2009).

World Health Organizatoin, Consolidated guidelines on the use of antiretroviral drugs for treating and preventing HIV infection: recommendations for a public health approach, World Health Organization, 155 pages (2016).

* cited by examiner

B)

METHOD FOR EPIGENETIC IMMUNE CELL DETECTION AND COUNTING IN HUMAN BLOOD SAMPLES

CROSS-REFERENCE TO RELATED APPLICATIONS

This application is a 35 U.S.C. § 371 national phase application of International Patent Application No. PCT/EP2019/067876, filed Jul. 3, 2019, which claims priority to German Patent Application No. 102018116353.3, filed Jul. 5, 2018, the entire disclosures of each of which are incorporated herein by reference in their entirety.

SEQUENCE LISTING

The Sequence Listing for this application is labeled "113828.000026_SequenceListing_US.txt", which was created on Dec. 22, 2020 and is 10 Kilobytes. The entire content is incorporated herein by reference in its entirety.

TECHNICAL FIELD

The present invention relates to methods for epigenetic blood and immune cell detection and counting in human blood samples, in particular for immunodiagnostics and newborn screening, and respective uses and kits.

BACKGROUND OF THE INVENTION

Quantitative abnormalities of lymphoid and myeloid immune cell subsets are indicative for several human diseases and therefore constitute important parameters for diagnosis and patient monitoring. Currently, immune cell quantification is mostly performed by flow cytometry (FCM), which provides flexibility with respect to the analyzed cell types and accuracy (1). However, although hematology analyzers used in diagnostic laboratories are highly developed and sample logistics are extensively adapted, FCM suffers from intrinsic limitations. FCM-based cell counting requires fresh, anti-coagulated or well-preserved blood samples with intact leukocytes. Even with fresh samples, it is advisable to work quickly since time-to-analysis can influence the results with cell deterioration beginning in the initial hours after blood draw. Time-to-analysis influences results due to cell deterioration within few hours after blood collection. Standardization remains a challenge due to biological, technical and operational variations (2-5) and standardized protocols remain to be established, especially for samples with low numbers of certain cell populations, e.g. in immunodeficiencies (6, 7). A critical challenge is that FCM-based cell counting requires intact leukocytes, but fresh or well-preserved blood is not available for all medical applications.

The most critical challenge, however, is that not all medical applications warrant availability of fresh or well-conserved blood samples and flow cytometry cannot be applied in these cases.

Therapeutic decisions for HIV-infected patients depend on $CD4^+$ T cell counting. At frequencies below 500 $CD4^+$ T cells/µl blood, antiretroviral therapy is recommended and becomes imperative below 200 cells/µl. In resource-poor regions, appropriate cell counting is hampered when blood collection and measurement cannot be performed in close succession. Therefore, treatment is initiated solely based on HIV-related clinical symptoms, which can result in suboptimal outcomes (8, 9). Furthermore, FCM is not applicable in newborn screening for severe, but treatable inborn defects, routinely performed on dried blood spots (DBS). Primary immunodeficiencies (PID) constitute such inborn disease group and are considered or are already part of screening programs (10). Typically, genetic defects lead to quantitative deficiencies of specific leukocyte subpopulations. Severe combined immunodeficiencies (SCID) represent such PID and are clinically characterized by the absence of T or B cells. Detection of SCID in newborns is currently based on quantitative PCR-assisted T cell receptor (TREC) and immunoglobulin kappa-deleting recombination excision circles (KREC) analyses (11). These methods reliably detect the lack of recent thymic T cell and bone marrow B cell emigrants, the predominant T and B cell subtypes present in neonatal blood. However, TREC/KREC analysis fails to detect other specific lymphocyte subsets defective in severe PID, such as Natural Killer (NK) cells or neutrophils. Despite this limitation, TREC newborn screening is effective and shows improved disease outcome due to earlier diagnosis (12). TREC analysis in newborn analysis is exclusively used for initial screening. Differential diagnosis and patient monitoring prior to and upon the curative hematopoietic stem cell transplantation requires change of technology and is performed by flow cytometry.

To overcome current technological and diagnostic limitations and to broaden applicability of immune monitoring, the inventors established DNA (un-)methylation-based, quantitative assessment of immune cells (epigenetic qPCR). This technique provides relative and absolute immune cell counts applicable to fresh, frozen or paper-spotted, dried blood. Signals are digital, i.e., indicating either one positive or negative value per cell rather than arbitrarily defined thresholds for "positiveness" as in FCM. It can be performed in an automated, operator-independent manner and reduces susceptibility to reagent variability, such as antibodies.

In a first aspect of the present invention, the above object is solved by a method for an improved methylation assay for identifying blood immune cells, comprising the steps of
  a) providing a sample of human blood, in particular from a newborn, comprising genomic DNA of blood immune cells;
  b) treating said genomic DNA of said immune cells with bisulfite to convert unmethylated cytosines into uracil;
  c) amplifying of said treated genomic DNA using suitable primer pairs to produce amplicons, and
  d) identifying said blood immune cells based on analyzing said amplicons as amplified,
  wherein said amplification and analysis comprises amplification and/or qPCR using primers and probes selected from at least one of the sets of SEQ ID NOs. 1 to 12 for CD4, SEQ ID NOs. 13 to 20 for CD8beta, SEQ ID NOs. 21 to 28 for LRP5, SEQ ID NOs. 29 to 36 for MVD, SEQ ID NOs. 37 to 44 for LCN2, and SEQ ID NOs. 45 to 56 for CD3gamma/delta, and
  wherein a demethylation of at least one CpG position in said amplicon is indicative for at least one blood immune cell selected from $CD3^+$ T cells, $CD4^+$ T cells, $CD8^+$ T cells, neutrophils, $CD14^+$ monocytes, CD56+ NK cells, and $CD19^+$ B cells.

Preferred is a method according to the present invention, further comprising an analysis of an amplicon for CD3 epsilon, as disclosed, for example, in US 2012-0107810.

Preferred is the method according to the present invention, further comprising an additional FCM of said blood immune cells to be identified.

Epigenetic immune cell counting provides a robust platform, capable of diagnosing immune defects, and optionally and conveniently complementing flow cytometry and T cell receptor excision circles analysis, nevertheless, without their respective limitations.

The present invention furthermore relates to the accurate quantification of methylation data as obtained using the above assay. This involves several components and considerations:

1. An internal standard, e.g. in silico converted plasmids.
2. A (e.g.) GAPDH normalizer in contrast to the methylated variant of a specific gene.
3. Thus, a comparison of all demethylated copies by the obligatory demethylated GAPDH with the specific (but present in the same number of copies) demethylated gene according to the quantification with 1.
4. Nevertheless, the above does not allow a truly "absolute" quantification, since the in silico converted standard does not correspond to the biological sample (which is converted only in the reaction vial.
5. Solving the problem at 4. based on adding and measuring a so-called GNoMs (Genomic Normaliser of Methylation), here, all original sequences are equimolarly included into a plasmid and then submitted to the overall process (bisulfite treatment and purification). Since they are present 1:1 a standard can be identified after the quantification using the standards in 1 showing the difference between in silico and in situ methylation. Using this factor, the methylation value of the measurements can be corrected, which improves the result considerably.
6. Using a defined amount of a nucleic acid (plasmid) with a standard gene having inverted CG bases, furthermore, any loss of material during the process can be accounted for, which further improves the method.
7. Reliable and specific assay components designed for clinical practice and needs.

Cell-type specific DNA methylation markers (13-15) amplified in qPCR potentially allow for immune cell detection and quantification even in samples of limited quantity and quality. The rationale for the identification of cell-type specific epigenetic markers has been described before (14, 16-18). Alternative methods for DNA methylation-based immune cell quantification include the analysis of individual CpG-sites on a genome-wide scale relying on microarray analysis (19). Such method allows estimation of leukocyte subpopulations based on calculated beta values (methylation intensities). The inventors assumed that locus-specific individualized epigenetic qPCR is highly specific and sensitive and thus well-suited for diagnostic approaches.

For epigenetic qPCR, genomic DNA is treated with bisulfite. Unmethylated CpG dinucleotides are converted to TpGs, whereas methylated CpGs remain unaltered. Thus, bisulfite conversion translates epigenetic marks into sequence information, allowing discrimination and quantification of both variants. Epigenetic qPCR is non-susceptible to loss of cell integrity since DNA is a stable substrate. It can be performed on fresh-frozen blood, DBS or other specimens without particular demands on preservation state. In addition, PCR components are synthetically produced and standardization is easy to achieve. Nevertheless, immune cell counting via epigenetic qPCR has not yet been demonstrated, due to absence of well-defined specific biomarkers and a lack of definitive and absolute quantification (20).

The inventors studied immune cell-type specific epigenetic qPCR for quantification of leukocyte populations in human blood. For total CD3+, CD4+ and CD8+ cytotoxic T cells (21, 22), regulatory elements in the genes coding for the cell type determining proteins were analyzed regarding their methylation status. Epigenetic markers for neutrophils, B and NK cells were identified from genome-wide discovery and profiling of resulting candidate genes.

Determination of absolute cell numbers (i.e., cells/µl blood) constitutes the gold standard, e.g. for counting of $CD4^+$ T cells in HIV patients. The inventors tested definitive and absolute counting of immune cells based on their cell-type specific epigenetic signals in healthy donors as well as a cohort of HIV patients and analyzed their equivalence to FCM. For DBS, where the blood volume is difficult to define, copies of unmethylated immune cell-type specific marker genes were related to copies of a universal denominator (GAPDH). Moreover, the diagnostic potential of epigenetic qPCR was demonstrated by identifying PID cases in a cohort of clinically inconspicuous newborns using DBS.

In a preferred embodiment of the method(s) according to the present invention, the method is integrated, and further comprises an analysis and a first normalization using a demethylation standard gene selected from a gene expressed in all cells to be identified, such as, for example, a housekeeping gene, such as, for example, GAPDH and beta-actin, preferably using primers and probes selected from SEQ ID NOs. 57 to 61 for the gene for said GAPDH.

In yet further preferred embodiment of the method(s) according to the present invention, the method is integrated, and further comprises a second normalization using an in silico bisulfite-converted recombinant nucleic acid comprising a sequence inversing all CpG dinucleotides to GpC of said at least one demethylation standard gene (GAP[GC] construct), preferably using primers and probes selected from SEQ ID NOs. 62 to 64 for said GAP[GC] construct.

In yet further preferred embodiment of the method(s) according to the present invention, the method is integrated, and further comprises a third normalization using a calibrator plasmid comprising one copy of each amplicon sequence in its unconverted genomic (i.e., unmethylated) state.

In yet further preferred embodiment of the method(s) according to the present invention, the method further comprises a quantification of said blood immune cells as identified.

In a preferred embodiment thereof, a method according to the present invention comprises a) providing a defined volume of a sample of human blood, in particular from a newborn, comprising (e.g. diploid) genomic DNA of blood cells to be quantitated;

b) providing an in silico bisulfite-converted recombinant nucleic acid comprising a demethylation standard gene, a sequence inversing all CpG dinucleotides to GpC of said demethylation standard gene, and a blood cell specific gene;

c) providing a recombinant nucleic acid comprising the demethylated genomic sequence of said demethylation standard gene of b), a sequence inversing all CpG dinucleotides to GpC of said demethylation standard gene, and said blood cell specific gene of b);

d) providing a recombinant nucleic acid comprising the sequence inversing all CpG dinucleotides to GpC of said at least one demethylation standard gene of b);

e) adding a defined amount of said recombinant nucleic acid of d) to said sample of a) ("spiking");

f) treating said (e.g. diploid) genomic DNA of the cells to be quantitated of a) and said recombinant nucleic acids of c) and d) with bisulfite to convert unmethylated cytosines into uracil;

g) amplifying of said nucleic acid molecules of a), b), c), and f) using suitable primer pairs to produce amplicons; and h) identifying the blood immune cells based on analyzing said amplicons, wherein said amplification and analysis comprises amplification and/or qPCR using primers and probes selected from at least one of the sets of SEQ ID NOs. 1 to 12 for CD4, SEQ ID NOs. 13 to 20 for CD8beta, SEQ ID NOs. 21 to 28 for LRP5, SEQ ID NOs. 29 to 36 for MVD, SEQ ID NOs. 37 to 44 for LCN2, and SEQ ID NOs. 45 to 56 for CD3gamma/delta, and wherein a demethylation of at least one CpG position in said amplicon is indicative for at least one blood immune cell selected from $CD3^+$ T cells, $CD4^+$ T cells, $CD8^+$ T cells, neutrophils, $CD14^+$ monocytes, CD56+ NK cells, and $CD19^+$ B cells.

Optionally, a quantification step for said blood immune cells is included, as described herein.

Preferred is the method according to the present invention, further comprising an analysis of an amplicon for CD3 epsilon as above.

Preferred is the method according to the present invention, further comprising an additional FCM of said blood immune cells to be identified.

Preferably, said demethylation standard gene is selected from a gene expressed in all cells to be detected, such as, for example, a housekeeping gene, such as, for example, GAPDH and beta-actin.

In one aspect of the method according to the present invention, more than one blood cell specific gene is analyzed, e.g. a panel of 1, 2, 3, 4, 5 or 6 blood cell specific genes is generated as needed or desired, optionally together with more than one demethylation standard gene as described herein Preferably, the nucleic acids are plasmids, e.g. linearized plasmids, such as bacterial plasmids, e.g. pUC, a yeast artificial chromosome (YAC), human artificial chromosome (HAC), PI-derived artificial chromosome (PAC), a bacterial artificial chromosome (BAC), and/or a PCR-product In an aspect of the method, the amplification is normalized using a first in silico bisulfite converted nucleic acid (plasmid), comprising a demethylation standard gene (e.g. GAPDH), an "artificial sequence" (the sequence inversing all CpG dinucleotides to GpC), as well as a blood cell specific gene (a "specific gene", e.g. CD4). All three elements are equally present (equimolar) on said nucleic acid, and are in silico bisulfite converted. Therefore, the normalization curve and the corresponding calibration curves can be directly compared with the sample, and the relative cell count can be determined from the ratio of blood cell specific gene to demethylation standard gene. Nevertheless, the nucleic acid does not correspond to the "real" sequence, since each C is replaced by a T. A serial dilution and determination of each concentration with all genes as mentioned generated the calibration curve for the assay.

In order to improve the accuracy of the approach, a second nucleic acid (plasmid) is used comprising the demethylation standard gene (e.g. GAPDH), the "artificial sequence" (the sequence inversing all CpG dinucleotides to GpC), and the blood cell specific gene (a "specific gene"). Nevertheless, these sequences are NOT in silico bisulfite converted, and correspond to the genomic sequences (in as far as the have a genomic counterpart, see below)—and thus can only be used for measuring the amplification (e.g. qPCR) efficiency.

The reason for the second standard is two-fold. A) For a definitive quantification a standard is required that is identical as in the biological sample to be analyzed (this is also a regulatory requirement). In the first nucleic acid, nevertheless, a double stranded AT-rich sequence is compared with a single-stranded U-rich sequence. Only the "true" bisulfite conversion of the double stranded nucleic acid allows for this definitive comparison. Then, the quotient of bisulfite conversion of blood cell specific gene to demethylation standard gene, normalized using the first nucleic acid, gives a factor of the efficiency. The same holds true for a quotient based on the division of the bisulfite conversion of the sequence inversing all CpG dinucleotides to GpC by the bisulfite conversion of the demethylation standard gene.

Preferably, the "artificial sequence" (the sequence inversing all CpG dinucleotides to GpC) is a random sequence comprising C and CpG sequences (for bisulfite conversion) that does not occur in the human genome. In one embodiment, the artificial sequence is the exact sequence of the part of GAPDH that is amplified (amplicon) wherein the CpG sequences are inverted into GpC sequences. The "artificial sequence" is found on all three nucleic acids as described above, namely on the first one (in silico bisulfite converted), the second one (for bisulfite conversion), and—as the only analyzed sequence—on the third nucleic acid (in silico bisulfite converted).

The third nucleic acid is given in a defined amount into a defined amount of blood, in particular from a newborn, and is then analyzed (e.g. purification, bisulfite treatment, second purification, desulfonation, specific amplification). Then, a normalization is performed against the first nucleic acid (how many copies were measured and given into the reaction), the efficiency is determined using a comparison with the second nucleic acid, and the (residual) copy number is determined using the third nucleic acid. Any losses are compared with a loss of genomic DNA that was subjected to the same procedure. The overall process allows for a precise definitive and absolute quantification of said DNA, and through this the cells in a blood sample, such as, for example, whole blood.

In one embodiment, the invention relates to an artificial sequence that is the exact sequence of the part of GAPDH that is amplified (amplicon) wherein the CpG sequences are inverted into GpC sequences as a tool when performing the method(s) of the present invention.

The composition of the cellular immune system holds valuable diagnostic information for various diseases. The standard technology for quantitative immune cell monitoring is flow cytometry. However, this method is limited to blood samples in which cell-integrity is retained. In clinical routine, this effectively restricts analysis to fresh blood samples as analytical substrate.

In order to widen the margin of use of diagnostic immune monitoring, the inventors implemented epigenetic qPCR systems for quantification of the major leukocyte populations. Upon determining immune cell type specific methylation marks, whole blood from 25 healthy donors, 97 HIV patients and 325 Guthrie cards from newborns including 25 cards from patients with primary immunodeficiencies (PID), including but not limiting to XLA, SCID, SCN, were analyzed. Methodological concordance between flow cytometric and epigenetic data for B-, NK-, total T cells, T helper cells, neutrophils, and cytotoxic T cells was determined and the ability of this new technique to identify quantitative immune cell deficiencies was tested.

Data show that quantification via epigenetic qPCR assays and flow cytometry perform equivalently in healthy subjects and HIV patients according to Bland-Altman testing. Epigenetic quantification is applicable for relative and absolute frequencies of leukocyte subsets in fresh and frozen blood samples. In contrast to flow cytometry, immune cell analysis of Guthrie cards accurately identifies cases PID in newborns. Epigenetic quantification of immune cell populations performs with high equivalence to standard flow cytometry offering a wider range of possible applications, including analysis of dried blood spots possibly laying a path to blood counting of patients in remote areas or from newborns.

Thus, preferred is the method according to the present invention, wherein said blood sample is selected from peripheral, capillary or venous blood samples or subfractions thereof, such as, for example, peripheral blood monocytes, blood clots, and dried blood spots. Also preferred is the method according to the present invention, comprising the step of diagnosing primary immunodeficiencies (PID) in a human, in particular a newborn, based on said quantification, wherein said sample preferably is a dried sample, like a Guthrie card (see also further below), or DBS (dried blood spots).

Preferred is a method according to the present invention, further comprising the step of concluding on the immune status of a human based on at least one quantification of said at last one immune cell type.

Preferred is the method according to the present invention, wherein said recombinant nucleic acid molecule is selected from a plasmid, a yeast artificial chromosome (YAC), human artificial chromosome (HAC), PI-derived artificial chromosome (PAC), a bacterial artificial chromosome (BAC), and a PCR-product.

Preferred is the method according to the present invention, wherein said demethylation standard gene is selected from a gene expressed in all cells to be detected, such as, for example, a housekeeping gene, such as, for example, GAPDH and beta-actin.

Preferred is the method according to the present invention, wherein said blood cell specific gene is selected from: A gene known or found to be expressed in all blood cells to be detected, CD4, CD8beta, and/or alpha, low-density lipoprotein receptor-related protein 5 (LRP5), mevalonate pyrophosphate decarboxylase (MVD), lipocalin-2 (LCN2), and the CD3gamma/delta region (gene).

Another aspect of the invention relates to a diagnostic kit, comprising materials for performing the method according to the present invention, optionally with instructions for use. Preferred materials are the nucleic acid molecules, and/or a bisulphite reagent. Preferred materials are selected from primers and probes selected from any one of SEQ ID NOs. 1 to 12 for the gene for CD4, SEQ ID NOs. 13 to 20 for the gene for CD8beta, SEQ ID NOs. 21 to 28 for the gene for LRP5, SEQ ID NOs. 29 to 36 for the gene for MVD, SEQ ID NOs. 37 to 44 for the gene for LCN2, SEQ ID NOs. 45 to 56 for the CD3gamma/delta genetic region, SEQ ID NOs. 57 to 61 for the gene for GAPDH, and SEQ ID NOs. 62 to 64 for the GAP[GC] construct.

Another aspect of the invention relates to the use of the kit according to the invention for performing a method according to the invention.

Yet another aspect of the invention then relates to a primer or probe selected from any one of SEQ ID NOs. 1 to 64, and an amplicon as amplified by a primer pair selected from SEQ ID NOs. 1 and 2; 3 and 4; 5 and 6; 7 and 8; 10 and 11; 13 and 14; 15 and 16; 18 and 19; 21 and 22; 23 and 24; 26 and 27; 29 and 30; 1 and 32; 34 and 35; 37 and 38; 39 and 40; 42 and 43; 45 and 46; 47 and 48; 49 and 50; 51 and 52; 54 and 55; 57 and 58; 59 and 60; and 62 and 63.

The present invention also encompasses a method for treating an immune-related disease in a human, in particular a newborn, patient in need thereof, comprising performing a method as described herein, and providing a treatment for said immune-related disease based on the results of said method. One additional embodiment comprises an immune cell monitoring, and immune-related diseases include, for example, PIDs, other immunodeficiencies or cancer.

Current immune cell monitoring requires fresh or well-conserved blood hampering diagnostics in medical fields where such substrates are unavailable. Here, the inventors describe immune cell-type specific epigenetic qPCR which allows determination of immune cell counts from unobservantly conserved, paper-spotted dried blood or fresh samples.

General feasibility of epigenetic qPCR has been shown previously using "Treg specific demethylated region (TSDR)" in T regulatory cells (13). Upon identification of specific epigenetic markers for a number of diagnostically relevant immune cell populations, the inventors demonstrate performance equivalence of the according epigenetic qPCR with the gold standard technologies (FCM, TREC/KREC analysis) of immune cell analytics. For this, the quantification of immune cells in fresh-frozen blood and/or DBS from healthy controls, a cohort of primary (PID) or acquired (HIV) immunodeficiencies, and a cohort of newborns with or without inborn immune deficiencies was analyzed.

Ideal DNA-methylation markers for cell type identification are discriminative between target (near 0% methylation) and all control cells (near 100% methylation). In addition to analysis of T cell associated genes CD3G/D, CD4, and CD8B, loci in the genes MVD, LRP5 and LCN2 were found to be unmethylated only in NK cells, B cells and neutrophils, respectively. MVD is a component of the mevalonate pathway (33), and is expressed in testis, duodenum and colon. LRP5 is involved in bone generation (34). LCN2 is an extracellular transport protein and a major protein of the human tear fluid (35). Reason and function of specific absence of methylation in these regions remains to be analyzed but does not affect its use for cell quantification in peripheral blood. All markers were validated by bisulfite sequencing and the discriminatory CpG-dinucleotides were selected for qPCR development and characterized on artificially generated methylated and unmethylated DNA. Quantitative amplification of target DNA was achieved without detecting background from non-target templates. qPCR assay performance was robust with low variation as shown by small intra and inter assay CVs in fresh, frozen, or dried blood.

For simultaneous quantification of different cell types in biological samples, the inventors designed a calibrator plasmid containing the unmethylated genomic sequences of GAPDH as reference quantifier and the cell type-specific markers. Whereas GAPDH was previously described as instable gene expression normalizer (36) and to contain segmental duplications (37), the GAPDH locus selected here is stably diploid and always unmethylated. Therefore, through adjusting the quantification of biological samples with the in silico bisulfite-converted standard and by the calibrator, assay specific technical inefficiencies can be corrected and allows definitive quantification (20) of the respective loci relative to unmethylated GAPDH, i.e., all nucleated cells. As such, epigenetic qPCR displays a direct proportional relation to cell types as determined by FCM. The remaining observed biases between the methods (38) may result from the biological and technical disparity between nucleic acid-based and antibody-based methods. Homogeneous error distribution and precision were comparable to data from previously performed method comparisons among different antibody-based methods (39). Together, these data suggest that epigenetic qPCR, both from liquid and dried blood substrates, performs equivalent to FCM for the relative quantification of immune cells.

With respect to clinical applications, relative cell quantification is accepted by WHO in HIV-treatment guidelines, but in medical practice treatment decisions depend on cell counting per volume (40, 41). For epigenetic qPCR, this poses a problem since DNA recovery is not quantitative and the relationship between DNA amount and blood volume is not fixed. For that reason, the inventors' experimental setup included the spiking of a defined concentration of artificial GAP[GC] into blood providing for an approximated inference to the original DNA content in a defined blood volume upon subsequent qPCR analysis. Whereas different efficiencies of genomic and plasmid DNA have been described (42), such differences are more reduced after bisulfite treatment and resulting genomic DNA fragmentation. When applied to healthy donors and a HIV cohort, the data showed high correlation and biases and limits of agreements similar to the data described for relative quantification method comparison. Accordingly, the inventors concluded that immune cell counting per microliter can be performed by epigenetic qPCR equivalent to FCM.

At present, neonatal screenings are always performed from DBS. Since FCM is not applicable to this substrate, TREC/KREC analysis is used for PID screening. Introducing epigenetic qPCR in such screening would therefore require equivalence testing to TREC/KREC. Due to different parameters tested, i.e., DNA excision circles vs. genomic DNA, method comparison is not feasible. Instead, the inventors estimated the specificity and sensitivity of TREC/KREC from (43). Epigenetic qPCR reliably identified newborns suffering from different types of PID with similar sensitivity and specificity when using the 99% confidence regions. It only failed to identify one newborn PID patient with maternal cell engraftment, i.e., a patient, where the absence of T and B cells is masked by maternal cells. Unlike the analysis of excision circles, epigenetic analysis is not limited to the main lymphocyte subsets. Such problems may be addressed by expanding the epigenetic qPCR portfolio to markers for memory T or B cells, which are absent in newborns without engraftment. When detected in newborn, such markers may allow detection of engraftment and thereby indicate the absence of a healthy inherent immune system.

Further quantitative defects of other immune cell populations occur in neutrophils and highly specialized Tregs. The inventors' data indicate that identification of such patients based on epigenetic qPCR for neutrophils and Tregs is possible early after birth, allowing for early diagnosis of SCN, which constitutes potentially life-threatening PIDs (43, 44).). The importance to detect and treat these severe immune disorders has been exemplified before (46).

Because of the scarceness of patients, conducting comprehensive studies of rare genetic diseases poses major challenges. Here, this limitation most affected the analysis of only six SCN patients, yet the set of SCID patients with different genetic backgrounds is well comparable to previously published studies (47). The limited set of data provided in this invention only proves technical feasibility but does not yet allow translation into newborn screening. Despite strict limitations of this invention, the inventors' data indicate that epigenetic qPCR may provide an option in medical screening procedures.

Taken together, the invention shows that epigenetic qPCR provides precise and accurate means for immune cell detection and monitoring, and it underscores that epigenetic qPCR may assist or even replace current immunodiagnostics in particular for unobservantly preserved blood or DBS.

The present invention will now be described and explained further in the following examples and figures, nevertheless, without being limited thereto. For the purposes of the present invention, all references as cited herein are incorporated by reference in their entireties.

TABLE 1

Cell-type specific epigenetic qPCR systems

Figure 1:
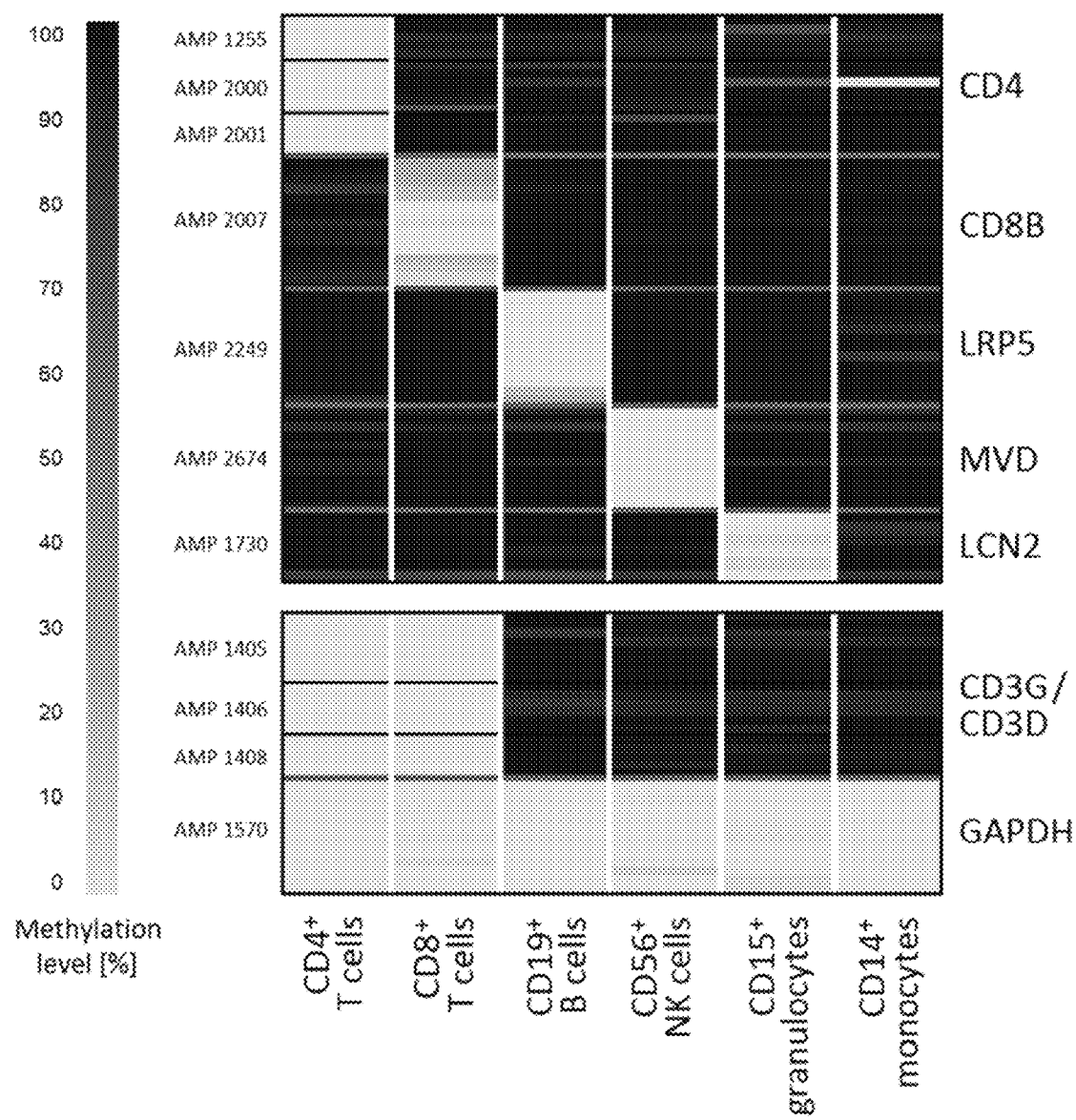
FIG. 1 shows the bisulfite sequencing derived DNA methylation of cell specific marker genes in purified immune cells. Immune cell types are arranged in columns with amplicons (AMP) and the associated gene names in rows. Different gene loci are separated by lines across columns, Amplicons within the same locus are separated by lines. Each individual row represents a single CpG site. Methylation rates are color-coded from light (0%) to dark (100%).

| Cell type specificity | Target gene of qPCR assay | Amplification system | Quantification mode | Plasmid based controls | | | Analyzed immune cell preparations | | | | | |
|---|---|---|---|---|---|---|---|---|---|---|---|---|
| | | | | TpG-variant | CpG-variant | calibrator | CD4+ T cells | CD8+ T cells | CD19+ B cells | CD56+ NK cells | CD15+ Granulocytes | CD14+ Monocytes |
| CD4+ T cells | CD4 | TpG-system [#TpG] | | 30100 | 0 | 6443 | 4795 | 244 | 50 | 58 | 61 | 57 |
| | | CpG-system [#CpG] | | 0 | 29650 | | 8 | 2300 | 7990 | 5100 | 5335 | 3600 |
| | | | RD$_{LS}$ [%] | 100 | 0 | | 99.8 | 9.6 | 0.6 | 1.1 | 1.1 | 1.6 |
| | | | RD$_U$ [%] | | | | 53.4 | 2.7 | 0.6 | 0.6 | 0.7 | 0.6 |
| | | | EF | | | 0.53 | | | | | | |
| | | | DD$_U$ [%] | | | | 91.4 | 6.1 | 0.6 | 1.1 | 1.3 | 1.4 |
| CD8+ T cells | CD8B | TpG-system [#TpG] | | 29850 | 0 | 10457 | 622 | 5845 | 51 | 36 | 37 | 19 |
| | | CpG-system [#CpG] | | 0 | 27150 | | 6400 | 608 | 11100 | 7375 | 7985 | 5720 |
| | | | RD$_{LS}$ [%] | 100 | 0 | | 8.9 | 90.6 | 0.5 | 0.5 | 0.5 | 0.3 |
| | | | RD$_U$ [%] | | | | 6.9 | 65.1 | 0.6 | 0.4 | 0.4 | 0.2 |
| | | | EF | | | 0.87 | | | | | | |
| | | | DD$_U$ [%] | | | | 7.3 | 90.6 | 0.4 | 0.4 | 0.5 | 0.3 |
| CD19+ B cells | LRP5 | TpG-system [#TpG] | | 30550 | 0 | 8723 | 2 | 2 | 9970 | 24 | 1 | 5 |
| | | CpG-system [#CpG] | | 0 | 31500 | | 4760 | 3205 | 1125 | 5105 | 5790 | 3655 |
| | | | RD$_{LS}$ [%] | 100 | 0 | | 0.0 | 0.1 | 89.9 | 0.5 | 0.0 | 0.1 |
| | | | RD$_U$ [%] | | | | 0.0 | 0.0 | 111.0 | 0.3 | 0.0 | 0.1 |
| | | | EF | | | 0.72 | | | | | | |
| | | | DD$_U$ | | | | 0.0 | 0.0 | 91.7 | 0.3 | 0.0 | 0.1 |
| CD56+ NK cells | MVD | TpG-system [#TpG] | | 27750 | 0 | 12400 | 150 | 169 | 170 | 10550 | 172 | 95 |
| | | CpG-system [#CpG] | | 0 | 25750 | | 9585 | 6850 | 16450 | 494 | 11200 | 7220 |
| | | | RD$_{LS}$ [%] | 100 | 0 | | 1.5 | 2.4 | 1.0 | 95.5 | 1.5 | 1.3 |
| | | | RD$_U$ [%] | | | | 1.7 | 1.9 | 1.9 | 117.5 | 1.9 | 1.1 |
| | | | EF | | | 1.03 | | | | | | |
| | | | DD$_U$ [%] | | | | 1.5 | 2.2 | 1.1 | 101.2 | 1.9 | 1.2 |

TABLE 1-continued

Cell-type specific epigenetic qPCR systems

| Cell type specificity | Target gene of qPCR assay | Amplification system | Quantification mode | Plasmid based controls TpG-variant | CpG-variant | calibrator | CD4+ T cells | CD8+ T cells | CD19+ B cells | CD56+ NK cells | CD15+ Granulocytes | CD14+ Monocytes |
|---|---|---|---|---|---|---|---|---|---|---|---|---|
| CD15+ Neutrophils | LCN2 | TpG-system [#TpG] | | 29100 | 0 | 4520 | 14 | 17 | 95 | 9 | 3230 | 65 |
| | | CpG-system [#CpG] | | 0 | 31400 | | 3485 | 2420 | 5170 | 3620 | 30 | 2110 |
| | | | $RD_{LS}$ [%] | 100 | 0 | | 0.4 | 0.7 | 1.8 | 0.2 | 99.1 | 3.0 |
| | | | $RD_U$ [%] | | | | 0.1 | 0.2 | 0.6 | 0.1 | 36.0 | 0.8 |
| | | | EF | | | 0.38 | | | | | | |
| | | | $DD_U$ [%] | | | | 0.4 | 0.6 | 1.7 | 0.2 | 94.7 | 2.2 |
| CD3+ T cells | CD3 d/G | TpG-system [#TpG] | | 33350 | 0 | 14133 | 12050 | 8320 | 37 | 59 | 28.8 | 23 |
| | | CpG-system [#CpG] | | 0 | 29450 | | 4 | 1 | 13800 | 9505 | 9125.0 | 6810 |
| | | | $RD_{LS}$ [%] | 100 | 0 | | 100.0 | 100.0 | 0.3 | 0.6 | 0.3 | 0.3 |
| | | | $RD_U$ [%] | | | | 112.8 | 112.1 | 0.2 | 0.6 | 0.3 | 0.3 |
| | | | EF | | | 1.17 | | | | | | |
| | | | $DD_U$ [%] | | | | 104.4 | 95.2 | 0.2 | 0.5 | 0.2 | 0.3 |
| Leukocytes | GAPDH | TpG-system [#TpG] | | | | 12050 | 9815 | 7425 | 15100 | 10110 | 8980 | 7655 |

Table 1. $RD_{LS}$: Relative unmethylation (locus speciifc) in %; $RD_U$: Relative unmethylation (universal) in %; EF: Efficiency factor; $DD_U$: definitive unmethylation (universal) in %

TABLE 2

Genetic defects and diagnostic classification by TREC/KREC and epigenetic qPCR for PID patients.

| | Disease Description | | | TREC/KREC Newborn Screening | | | Epigenetic qPCR Analysis (CD3 G/D, GAPDH)[3] Conspicuous [yes/no] | (MVD, GAPDH)[3] Conspicuous [yes/no] | (LRP5, GAPDH)[3] Conspicuous [yes/no] | |
|---|---|---|---|---|---|---|---|---|---|---|
| Identifier | Classification | Gene Defect | Loss of Function Type | TREC[1] Positive [yes/no] | KREC[2] Positive [yes/no] | Screening Classification | | | | Screening Classification |
| 1 | SCID | ADA | amorph | yes | yes | correctly identified | yes | yes | yes | correctly identified |
| 2 | SCID | ADA | amorph | no | yes | correctly identified | yes | yes | yes | correctly identified |
| 3 | DO-SCID[4] | ADA | hypomorph | no | yes | correctly identified | no | yes | yes | correctly identified |
| 4 | DO-SCID[4] | ADA | hypomorph | no | yes | correctly identified | yes | yes | yes | correctly identified |
| 5 | SCID | AK2 | amorph | yes | no | correctly identified | yes | yes | yes | correctly identified |
| 6 | SCID | AK2 | amorph | yes | yes | correctly identified | yes | yes | no | correctly identified |
| 7 | SCID | Artemis | amorph | yes | yes | correctly identified | yes | yes | yes | correctly identified |
| 8 | SCID | CD3D | amorph | yes | no | correctly identified | yes | yes | no | correctly identified |
| 9 | SCID w ME[5] | IL2RG | amorph | yes | no | correctly identified | no | no | no | not identified |
| 10 | SCID | IL2RG | amorph | yes | no | correctly identified | yes | yes | yes | correctly identified |
| 11 | SCID | IL7RA | amorph | yes | no | correctly identified | yes | no | no | correctly identified |
| 12 | SCID | IL7RA | amorph | yes | no | correctly identified | yes | yes | yes | correctly identified |
| 13 | SCID | IL7RA | amorph | yes | no | correctly identified | yes | yes | yes | correctly identified |
| 14 | DO-SCID[4] | JAK3 | hypomorph | no | no | not identified | yes | yes | yes | correctly identified |
| 15 | SCID | PNP | amorph | yes | yes | correctly identified | yes | yes | yes | correctly identified |
| 16 | SCID | PNP | amorph | yes | yes | correctly identified | yes | yes | yes | correctly identified |
| 17 | SCID | RAG1 | hypomorph | yes | yes | correctly identified | yes | yes | no | correctly identified |
| 18 | SCID | RAG1 | amorph | yes | yes | correctly identified | no | yes | yes | correctly identified |
| 19 | SCID | RAG2 | amorph | yes | yes | correctly identified | yes | no | yes | correctly identified |
| 20 | XLA | BTK | amorph | no | yes | correctly identified | yes | no | yes | correctly identified |
| 21 | XLA | BTK | amorph | no | yes | correctly identified | no | no | yes | correctly identified |
| 22 | XLA | BTK | amorph | no | yes | correctly identified | no | no | yes | correctly identified |
| 23 | XLA | BTK | amorph | no | yes | correctly identified | yes | yes | yes | correctly identified |
| 24 | XLA | BTK | hypomorph | no | no | not identified | no | yes | yes | correctly identified |

Figure 5:
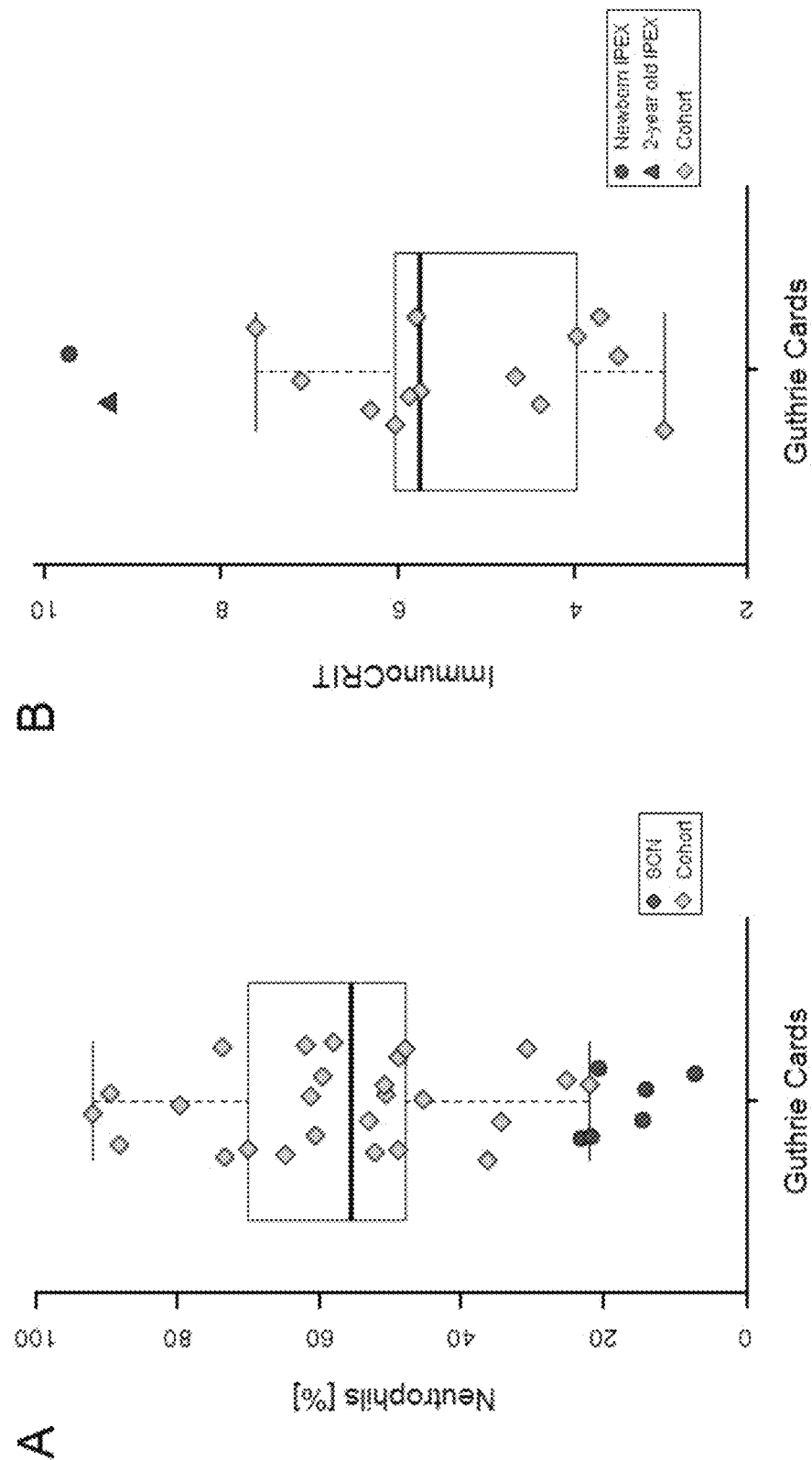
FIG. 5 shows the epigenetic qPCR on DBS from newborns with SCN. DBS from healthy controls and newborns with confirmed SCN were subjected to epigenetic qPCR for quantification of $CD15^+$ neutrophils. Healthy cohorts are represented in the boxplot and results from diseased patients are depicted.

[1]TREC values ≤6 copies per dot were considered positive;
[2]KREC values ≤4 copies per dot were considered positive;
[3]Values outside the joint 99% reference range were considered conspicious, see FIG. 5;
[4]Delayed onset SCID;
[5]SCID with maternal engraftment

TABLE 3

Selected candidate regions for neutrophils, NK and B cells from genome-wide discovery on Illumina's Infinium methylation-specific array. DNA methylation marker candidates for NK cells, B lymphocytes and neutrophils identified from a genome-wide discovery experiment using Illumina's 450k Infinium human methylation bead chip array are shown. Bisulfite converted gnomic DNA from purified immune cell populations (as specified in the table's header, each from two independent healthy donors A and B) was used for a genome-wide DNA methylation analysis applying Illumina's 450k Infinium human methylation bead chip array. The assay interrogates 450,000 methylation sites quantitatively across the genome at single-nucleotide resolution. From measured signal intensities, beta values were calculated representing the degree of methylation at a locus. The table shows calculated beta values of 6 loci (as indicated by CpG site ID acc. to Illumina 450k micro array) that are associated with genes MVD, LRP5 or LCN2.

| | | Tested immune cell populations | | | | | | | | | | |
|---|---|---|---|---|---|---|---|---|---|---|---|---|
| CpG site ID (acc. To Illumina 450k micro array) | Associated gene | CD4+ T cells CD 3 + CD4+ CD45RA+ CCR7+ | | CD8+ T cells CD3+ CD8+ CD45RA+ CCR 7+ | NK cells CD5 6+ CD 16−/dim | | | B cells CD 19+ | | Monocytes CD 14++ | | Neutrophil granulocytes CD 15++ CD 16++ | |
| | | A | B | A | A | B | C | A | B | A | B | A | B |
| cg05355684 | MVD | 0.90 | 0.92 | 0.91 | 0.10 | 0.08 | 0.08 | 0.92 | 0.92 | 0.92 | 0.89 | 0.90 | 0.91 |
| cg27467516 | MVD | 0.79 | 0.84 | 0.85 | 0.52 | 0.51 | 0.48 | 0.82 | 0.86 | 0.84 | 0.84 | 0.82 | 0.82 |
| cg13738327 | LRP5 | 0.97 | 0.96 | 0.97 | 0.97 | 0.97 | 0.97 | 0.02 | 0.04 | 0.97 | 0.98 | 0.98 | 0.98 |
| cg00464927 | LRP5 | 0.99 | 0.99 | 0.97 | 0.95 | 0.96 | 0.97 | 0.04 | NA | 0.97 | 0.97 | 0.98 | 0.99 |
| cg14615559 | LCN2 | 0.73 | 0.89 | 0.85 | 0.84 | 0.85 | 0.88 | 0.83 | 0.88 | 0.71 | 0.66 | 0.04 | 0.04 |
| cg22438810 | LCN2 | 0.70 | 0.87 | 0.86 | 0.74 | 0.75 | 0.79 | 0.74 | 0.79 | 0.80 | 0.82 | 0.17 | 0.19 |

TABLE 4

Data from method comparison analysis. Pearson coefficients, bias and precision from the comparison of epigenetic qPCR and flow cytometry performed on blood samples from 97 HIV+ patients (liquid; spotted and dried on Guthrie cards, DBS) are presented.

| | | Analysis of CD3+ T cells | Analysis of CD4+ T cells | Analysis of CD8+ T cells |
|---|---|---|---|---|
| Scatter plot analysis | Pearson coefficient r (p-Value) | | | |
| | FCM vs. epigen. qPCR (blood) | 0.977 (p < 0.001) | 0.957 (p < 0.001) | 0.966 (p < 0.001) |
| | FCM vs. epigen. qPCR (DBS) | 0.953 (p < 0.001) | 0.742 (p < 0.001) | 0.924 (p < 0.001) |
| | Epigen. qPCR (blood) vs. epigen. qPCR (DBS) | 0.954 (p < 0.001) | 0.792 (p < 0.001) | 0.951 (p < 0.001) |
| Bland-Altman analyis | Bias [%] (95% C.I.) | | | |
| | FCM vs. epigen. qPCR (blood) | 4.32 (3.48, 5.16) | −6.59 (−8.48, −4.70) | 10.27 (8.95, 11.59) |
| | FCM vs. epigen. qPCR (DBS) | −0.16 (−1.43, 1.10) | −42.58 (−46.07, −39.08) | −1.15 (−3.03, 0.73) |
| | Epigen. qPCR (blood) vs. epigen. qPCR (DBS) | −4.45 (−5.70, −3.21) | −35.83 (−8.69, −32.98) | −11.00 (−12.58, −9.42) |
| | Precision [%] (95% C.I.) | | | |
| | FCM vs. epigen. qPCR (blood) | 8.12 (6.94, 9.31) | 17.63 (14.96, 20.31) | 12.73 (10.86, 14.60) |
| | FCM vs. epigen. qPCR (DBS) | 12.43 (10.64, 14.22) | 32.98 (28.04, 37.93) | 18.32 (15.66, 20.98) |
| | Epigen. qPCR (blood) vs. epigen. qPCR (DBS) | 12.05 (10.29, 13.80) | 27.07 (23.04, 31.11) | 15.21 (12.98, 17.44) |

TABLE 5

Stability testing of DBS. T cell subpopulations measured by epigenetic qPCR analysis from blood, spotted, dried on Guthrie cards and stored for various times and at different temperatures.

| Storage condition | | CD3+ T cells Mean [%] | Standard Deviation [%] | CD4+ T cells Mean [%] | Standard Deviation [%] | CD8+ T cells Mean [%] | Standard Deviation [%] |
|---|---|---|---|---|---|---|---|
| 1 day | 4° C. | 20.94 | 0.62 | 18.85 | 0.36 | 5.73 | 0.51 |
| | Room temperature | 21.19 | 1.07 | 17.87 | 2.39 | 5.22 | 0.13 |
| | 37° C. | 24.36 | 1.64 | 22.21 | 4.29 | 5.94 | 0.64 |
| 1 week | 4° C. | 27.46 | 3.88 | 21.11 | 1.28 | 7.14 | 2.24 |
| | Room temperature | 24.21 | 0.50 | 23.87 | 2.50 | 7.39 | 0.75 |
| | 37° C. | 24.41 | 2.32 | 21.42 | 0.86 | 7.14 | 0.26 |
| 6 weeks | 4° C. | 21.56 | 3.38 | 22.78 | 5.26 | 6.19 | 0.80 |
| | Room temperature | 24.09 | 3.44 | 19.76 | 6.24 | 7.62 | 2.54 |
| | 37 ° C. | 22.91 | 1.42 | 21.34 | 1.23 | 5.98 | 0.39 |

TABLE 6

Epigenetic qPCR from DBS spotted with diluted blood. The three main T cell subpopulations were measured by epigenetic qPCR in different concentrations from a dilution series of EDTA-blood samples.

|  | CD3+ T cells Mean [%] | Standard Deviation [%] | CD4+ T cells Mean [%] | Standard Deviation [%] | CD8+ T cells Mean [%] | Standard Deviation [%] |
|---|---|---|---|---|---|---|
| Donor A undiluted | 22.46 | 0.00 | 15.20 | 0.00 | 8.43 | 0.00 |
| 1:3 dilution | 19.89 | −11.42 | 12.01 | −20.97 | 5.84 | −30.80 |
| 1:9 dilution | 19.49 | −13.22 | 16.45 | 8.21 | 7.26 | −13.97 |
| 1:27 dilution | 15.90 | −29.21 | NA | NA | NA | NA |
| Donor B undiluted | 19.39 | 0.00 | 20.92 | 0.00 | 5.70 | 0.00 |
| 1:3 dilution | 17.27 | −10.96 | 17.60 | −15.88 | 4.03 | −29.31 |
| 1:9 dilution | 18.64 | −3.90 | 21.60 | 3.22 | 5.39 | −5.46 |
| 1:27 dilution | 15.88 | −18.08 | 23.10 | 10.41 | NA | NA |
| Donor C undiluted | 12.40 | 0.00 | 10.86 | 0.00 | 4.09 | 0.00 |
| 1:3 dilution | 12.45 | 0.45 | 11.18 | 2.89 | 3.29 | −19.59 |
| 1.9 dilution | 8.61 | −30.57 | 10.45 | −3.76 | 5.50 | 34.33 |
| 1:27 dilution | 23.11 | 86.42 | NA | NA | NA | NA |

TABLE 7

Oligonucleotides used for bisulfite sequencing and qPCR and their respective concentrations as used in the reactions.

Oligonucleotides for bisulfite sequencing

| Gene | ENSEMBL-ID | Amp | Sequence (5'-3') | SEQ ID No. | Conc. [µM] |
|---|---|---|---|---|---|
| CD4 | ENSG00000010610 | 1255 | Fw. GGTTTAGGAGGGGTTGTATATT | 1 | 0.5 |
|  |  |  | Rev. GGTTTAGGAGGGGTTGTATATT | 2 | 0.5 |
| CD4 | ENSG00000010610 | 2000 | Fw. GGGTTAGAGTTTAGGGTTGTT | 3 | 0.5 |
|  |  |  | Rev. ACTATCCCCAATATCCTCTACTT | 4 | 0.5 |
| CD4 | ENSG00000010610 | 2001 | Fw. TCTAAAATATACAAAACTAACCCAAT | 5 | 0.5 |
|  |  |  | Rev. GTGTTAGATAGAGTTTGGGGGT | 6 | 0.5 |
| CD8B | ENSG00000172116 | 2007 | Fw. AATGTTTTATTTGGGGGTTTAT | 13 | 0.5 |
|  |  |  | Rev. CCTACTACTCCTTCAATTCTCAA | 14 | 0.5 |
| LRP5 | ENSG00000162337 | 2249 | Fw. ATTTTTGTGTGATTTTAGGGTT | 21 | 0.5 |
|  |  |  | Rev. ATATCCAAATATCCTACCCTCC | 22 | 0.5 |
| MVD | ENSG00000167508 | 2674 | Fw. AACCCTAATTTCCTTCTTACT | 29 | 0.5 |
|  |  |  | Rev. GGTGTGGGTTTGAGTTTATTT | 30 | 0.5 |
| LCN2 | ENSG00000148346 | 1730 | Fw. GATTAGGTTTGAGGTGGAGTT | 37 | 0.5 |
|  |  |  | Rev. TATCCCTACCAAAAATACAACA | 38 | 0.5 |
| CD3G/D | ENSG00000160654 ENSG00000167286 | 1405 | Fw. GATTTTTAGATGTTTGGGGTT | 45 | 0.5 |
|  |  |  | Rev. TTATTCCACCTATTACCTTCCA | 46 | 0.5 |
| CD3G/D | ENSG00000160654 ENSG00000167286 | 1406 | Fw. TTTAGGTTGTGTGTAAATGTGG | 47 | 0.5 |
|  |  |  | Rev. ATAAACCTCACTCCCATCAATA | 48 | 0.5 |
| CD3G/D | ENSG00000160654 ENSG00000167286 | 1408 | Fw. AGGATGAGGATAGTTAGGTTTTT | 49 | 0.5 |
|  |  |  | Rev. AATCCCTCCTAAATTCATTACC | 50 | 0.5 |

TABLE 7-continued

Oligonucleotides used for bisulfite sequencing and qPCR and their respective concentrations as used in the reactions.

| GAPDH | ENSG 00000111640 | Fw. | AAACCCACTTCTTTAATTTACC | 57 | 0.5 |
|---|---|---|---|---|---|
| | | Rev. | TGGGGGTAGGGTAGTTG | 58 | 0.5 |
| GAP [GC] | — | | | | |

Oligonucleotides for qPCR analysis

| Gene | Assay variant | | Sequence (5'-3') | SEQ ID No. | Conc. [µM] |
|---|---|---|---|---|---|
| CD4 | TpG | | | | |
| | | Fw. | CCCTACTCTTATAATAAACATTTTTATCAA | 7 | 4.5 |
| | | Rev. | GAAATTATTTTTGAGTGTTTTTAATG | 8 | 3 |
| | | Probe | TGATTTTGAGGGTGGTGGTTATTTTG | 9 | 0.25 |
| CD4 | CpG | | | | |
| | | Fw. | CCCTACTCTTATAATAAACATTTTTATC | 10 | 1.5 |
| | | Rev. | GGAAATTATTTTTCGAGTGTTTTTAACG | 11 | 1.5 |
| | | Probe | ATTTTGAGGGCGGCGGTTATTTT | 12 | 0.25 |
| CD8B | TpG | | | | |
| | | Fw. | GTGGTTAAGAAATTAATAGGAAAAAGAATG | 15 | 1.5 |
| | | Rev. | CTTCCCCACCACAATACAACA | 16 | 1.5 |
| | | Probe | TGTTTGTGAGGTATTTAGTTGATGGGAGTTT | 17 | 0.125 |
| CD8B | CpG | | | | |
| | | Fw. | GGTTAAGAAATTAATAGGAAAAAGAAC | 18 | 1.5 |
| | | Rev. | CCCCATATTACTTCCCCG | 19 | 1.5 |
| | | Probe | CGTTTGTGAGGTATTTAGTCGACGGGAG | 20 | 0.125 |
| LRP5 | TpG | | | | |
| | | Fw. | AATATTACAACCATACACCCAACAA | 23 | 1.5 |
| | | Rev. | AAGTGATAGAATTTTATGTTTTTTTTATG | 24 | 1.5 |
| | | Probe | TTAGTTGAGGTGAGGTGTTTTGTTAGT | 25 | 0.25 |
| LRP5 | CpG | | | | |
| | | Fw. | ATTAATATTACGACCGTACGC | 26 | 1.5 |
| | | Rev. | CGATAGAATTTTACGTTTTTTTAC | 27 | 1.5 |
| | | Probe | ACGAAACGCCTCGCCTCGA | 28 | 0.25 |
| MVD | TpG | | | | |
| | | Fw. | GGTTTTGTGGTATTTTTATAGAGTAGT | 31 | 1.5 |
| | | Rev. | CCATATACACCCTCCTCAA | 32 | 1.5 |
| | | Probe | CCCTAAACCACCTCTTCCCCTACAC | 33 | 0.125 |
| MVD | CpG | | | | |
| | | Fw. | TTTTGTGGTATTTTTATAGAGTAGC | 34 | 1.5 |
| | | Rev. | CCATATACGCCCTCCTCG | 35 | 1.5 |
| | | Probe | AAACCGCCTCTTCCCCTACG | 36 | 0.25 |
| LCN2 | TpG | | | | |
| | | Fw. | ACCAAAAATACAACACTTCAA | 39 | 1.5 |
| | | Rev. | GGTAATTGTTAGTAATTTTTGTG | 40 | 1.5 |
| | | Probe | CACTCTCCCCATCCCTCTATC | 41 | 0.15 |
| LCN2 | CpG | | | | |
| | | Fw. | TACCAAAAATACAACACTCCG | 42 | 1.5 |
| | | Rev. | AGGTAATTGTTAGTAATTTTTACG | 43 | 1.5 |
| | | Probe | CTCACTCTCCCCGTCCCTCTATC | 44 | 0.15 |
| CD3G/D | TpG | | | | |
| | | Fw. | CCTAAACACTACCACATCTCAA | 51 | 1.5 |
| | | Rev. | AGAAATTTAGTTGTTATGGTTTGT | 52 | 1.5 |
| | | Probe | AAAAAACCATCAACCCCATAACACAAA | 53 | 0.25 |
| CD3G/D | CpG | | | | |
| | | Fw. | CTAAACACTACCACATCTCGA | 54 | 1.5 |
| | | Rev. | AAATTTAGTTGTTACGGTTTGC | 55 | 1.5 |
| | | Probe | CCGTCGACCCCATAACGC | 56 | 0.25 |
| GAPDH | TpG | | | | |
| | | Fw. | GGTTTTTGGTATTGTAGGTTTT | 59 | 1.5 |
| | | Rev. | CCAATTACAACATAACAACCA | 60 | 1.5 |
| | | Probe | TGTTTGGATGTTGTGTTTGTGGTAGAGTG | 61 | 0.25 |

TABLE 7-continued

Oligonucleotides used for bisulfite sequencing and qPCR and their respective concentrations as used in the reactions.

| GAP [GC] | TpG | | | |
|---|---|---|---|---|
| | Fw. | GGTTTTGTGTATGTTAGGTTTG | 62 | 0.75 |
| | Rev. | CCACATTACAACATAAACACAC | 63 | 0.75 |
| | Probe | TGTTGTGATGTTGGTTTTGGTGTAGAGGT | 64 | 0.125 |

EXAMPLES

Study Design—The research objective was to determine if epigenetic qPCR can complement current methods for diagnostic immune cell counting. To test this, the inventors identified and evaluated cell-type specifically unmethylated DNA loci, for relevant immune cells including CD15$^+$ neutrophils, CD19$^+$ B, CD56$^+$ NK, CD3$^+$, CD4$^+$ and CD8$^+$ T cells and Tregs. Epigenetic qPCR was developed and standardized using established normalization parameter. Critical steps for this normalization were to provide for comparable measurement for all cell-specific qPCRs by adjusting for qPCR efficiency between different genomic loci and different bisulfite conversion effects of different regions as well as normalization for DNA purification efficiency for absolute quantification of cells per blood volume. Both, relative and absolute quantification was applied to evaluate whole blood from 25 healthy donors, 97 HIV patients, as well as dried spots from 250 dried blood spots from healthy newborn and 24 newborns cards from newborn patients with primary immunodeficiencies. Results of epigenetic qPCR were verified for equivalence to standard FCM and furthermore tested in applications with current diagnostic undersupply in immune cell counting, in particular primary and acquired immune deficiencies. Patient material was provided from German and Californian hospitals and blinded prior to data analysis.

Dried blood spots—Three 3.2 mm DBS punches of genetically confirmed IPEX, SCID, SCN and XLA patients, from 250 randomly selected anonymous newborns and from capillary blood of one patient with confirmed IPEX were obtained. The sequencing and genetic confirmation of the included PID patients was performed in compliance with the practitioner toolkit of the Clinical Sequencing Exploratory Research (CSER) Consortium. Written parental consent was obtained for all participants. The study was approved by the Medical Association Chamber of Saxony ethics committee or institutional review board at University of Freiburg, Germany.

Peripheral whole blood—EDTA-anticoagulated peripheral blood was collected from 25 healthy subjects and 97 HIV patients under treatment at Leipzig University with ethical consent. Samples were subjected to epigenetic qPCR and to standard FCM (48). Information was blinded to experimenters.

DNA preparation and bisulfite conversion—For purified cells, genomic DNA was isolated and bisulfite treated using DNeasy tissue and EpiTect Fast Bisulfite conversion kits (Qiagen, Hilden, Germany) according to the manufacturer's instructions. For EDTA-blood, 20 μl substrate was supplemented with 16 μl lysis buffer, 3 μl proteinase K (30 mg/mL) and GAP[GC] plasmid (final concentration 20,000 copies/μl) and lysed for 10 minutes at 56° C. For conversion, EpiTect Fast Bisulfite Conversion Kit was used. 3×3.2 mm DBS punches were added to 68.75 μl lysis buffer, 10.75 μl proteinase K (30 mg/mL), 20,000 copies/μl GAP[GC] plasmid (final concentration) and lysed for 60 minutes at 56° C. Conversion was performed for 45 min at 80° C. adding 180 μl ammonium bisulfite (68%-72%, pH 4.8-5.3, Chemos AG, Munich, Germany) and 60 μl tetrahydrofuryl alcohol (Sigma-Aldrich). For purification "My Silane Genomic DNA kit" (Invitrogen, Carlsbad, CA) was used following manufacturer's instructions. Bisulfite conversion rates were analyzed previously and are provided in the manufacturer's manual with values above 98% (49). Efficiency of conversion was routinely checked by bisulfite sequencing showing rates above 98%. As process control, the genomic calibrator included conversion controls in each individual qPCR. BioPerl was used for in silico bisulfite conversion of sequences (50).

Epigenetic qPCR—Thermal cycling was done as follows: 1×95° C. for 10 or 35 min followed by 50×95° C. for 15 sec, and 61° C. for 1 min in 5 μl (DBS) or 10 μl (EDTA-blood) using Roche LightCycler 480 Probes Master. For calculation of cell numbers from autosomal genes, a 2:1 allel-to-cell ratio was assumed. For $RD_{1s}$ [%], TpG-copies were divided by TpG-+CpG-copies. For $RD_u$[%], the quotient of TpG copies (of the respective immune cell type) and GAPDH copies was calculated. For $DD_u$[%], $RD_u$ were corrected by EF compensating for performance differences between different qPCRs. For assay-specific EF, the inventors used a plasmid-based calibrator harboring the genomic target region of all qPCRs, including GAPDH (universal denominator) and an artificial GAP[GC] region. The calibrator was subjected to bisulfite conversion followed by qPCR. EF was calculated by dividing measured TpG copies by parallelly measured GAPDH copies. EFs were derived from approximately 25 experiments. 95% CI were 0.90-1.19 (CD3G/D), 0.47-0.63 (CD4), 0.75-1.00 (CD8B), 0.58-0.77 (LRP5), 0.89-1.18 (MVD) and 0.38-0.48 (LCN2). For absolute quantification, an artificial GAPDH sequence inversing all CpG dinucleotides to GpC (GAP[GC]) and its corresponding epigenetic qPCR were designed without cross reactivity with endogenous GAPDH. EF for GAP[GC] was 0.87 with an 95% CI of 0.75-1.00.

Combined TREC/KREC newborn screening assay—TREC/KREC screening was applied as described previously (51). Briefly, DNA from one 3.2-mm punch of the original DBS was extracted in a 96-well format, and quantitative triplex real-time qPCR for TREC, KREC, and β-actin (ACTB) was performed using a ViiA7 Real-Time PCR System (Applied Biosystems, Foster City, CA, USA). TREC and KREC copy numbers were determined per 3.2-mm punch. ACTB was used to verify suitable DNA amounts per DBS and not for normalizing TREC/KREC copies.

Plasmids—Sequences, corresponding to methylated or unmethylated, bisulfite-converted genomic regions, were designed in silico and inserted into plasmid pUC57 (Genscript Inc., Hongkong, China) and used for assay establishment and as qPCR quantification standard. Standard plasmids harbor all assay target sequences equimolarly. Plasmids were spectrophotometrically quantified, linearized by ScaI and serially diluted in 10 ng/µl of λ-phage DNA (New England Biolabs) to obtain 31250, 6250, 1250, 250, 50 or 30 copies in the final reaction. Calibrator plasmid harbors all assay target sequences equimolarly in genomic unconverted, unmethylated version. Artificial spike-in plasmid carries unconverted GAPDH with inverted CpG dinucleotides (GAP[GC]).

Oligonucleotides—Oligonucleotides (Metabion AG, Munich, Germany) are described in Table 7.

Flow cytometry—For leukocyte purification, peripheral blood from healthy adult donors was fractionated by FCM into $CD15^+$, $CD14^+$, $CD56^+$ NK, $CD19^+$ B, $CD4^+$ and $CD8^+$ T cells with cell purities >97% and viability >99% as described previously (13). For analytical cell quantification, absolute $CD45^+$ leukocyte counts were determined by a MACSQuant cytometer (Milteny Biotec, Bergisch Gladbach, Germany). Frequencies and absolute counts of $CD15^+$ neutrophils, $CD19^+$ B, $CD56^+$ NK, $CD3^+$, $CD4^+$ and $CD8^+$ T cells and $FOXP3^+$ Tregs were calculated as previously described (13, 48).

Statistical analysis—CP (crossing point) of triplicate measurements was computed by second-derivative maximum applying LC480 software (Roche, Mannheim, Germany) to yield copy numbers (plasmid units) by interpolating amplification (f) from calibration curves generated with serial dilutions of plasmid-based standards. Sample sizes for method comparison were chosen as 100 to provide 95% CI for limits of agreement at +/−0.34× the underlying standard deviation. Estimation of reference ranges demands a healthy population of at least 120 individuals for the nonparametric estimation of the 95% CI. The number of healthy cases was increased until exhaustion of available samples to accommodate for multidimensionality and estimation of extreme quantiles. Henze-Zinkler test was used to check for multivariate normality. Method comparison between flow cytometric and qPCR-based measuring technique was done as follows: Bivariate data from the two methods were illustrated in a scatterplot. Linear regression was performed testing a) for a slope different from 1 and b) an intercept different from 0. Bland-Altman plots were inspected analyzing bias and precision statistics (29). Acceptable precision was regarded as average deviation from the bias in percent. The limit of quantification for qPCR assays defined by the inter assay CV (0.2) was used as precision criterion and acceptable limits of agreement of 0.4. Wilcoxon-Rank-Sum Test was used to for median differences. The estimated bias, precision statistic and respective 95% CI are reported. For correlation, Pearson product-moment correlations were used. All p-values are two-sided. Statistics software R 3.3.0 was employed.

Cell type-specific bisulfite-conversion—Methylation-dependent conversion of CpG-dinucleotides was analyzed by bisulfite sequencing (24) aiming at marker identification for immune cell populations from human peripheral blood. Candidate loci were selected from literature or discovered using Illumina's 450k array-based assay. The inventors' data showed distinctive absence of methylation at individual CpG positions for $CD56^+$ NK cells, $CD19^+$ B cells and neutrophils (target cell types), whereas the same CpGs were methylated in control cell types (Table 3). Based on these findings, amplicons (AMP) were designed for denser CpG methylation analysis in the identified regions. As a likely candidate marker for $CD4^+$ T cells, the inventors designed three AMPs for bisulfite sequence analysis covering regulatory elements within the 5' region of the first intron (AMPs 1255, 2000 and 2001) in the CD4 gene (21, 22). Unmethylated CpG-sites are detected as TpG residues after bisulfite-conversion and amplification occurs exclusively in target cells, i.e., $CD4^+$ T lymphocytes. The same CpGs were inert to bisulfite-conversion in control cell types, including $CD56^+$ NK cells, $CD8^+$ T lymphocytes, $CD14^+$ monocytes, $CD19^+$ B lymphocytes and $CD15^+$ granulocytes (FIG. 1). Next, the inventors investigated the CD8B gene as a potential epigenetic marker for $CD8^+$ T cells (21, 22) by designing amplicons targeting regulatory elements within its third intron (AMP2007). Here, bisulfite-mediated conversion of CpGs was observed exclusively in $CD8^+$ T cells, while those CpGs were inert to conversion in control cells. According epigenetic marks were identified for B cells, NK cells and neutrophils in the genes coding for low-density lipoprotein receptor-related protein 5 (LRP5, AMP2249), mevalonate decarboxylase (MVD, AMP2674) and lipocalin 2 (LCN2, AMP1730), respectively. Each AMP was uniquely unmethylated in the target cell type and fully methylated in the corresponding control leukocyte populations (FIG. 1). DNA methylation of the intergenic CD3G and CD3D region (AMPs 1405, 1406 and 1408), constituting a marker for $CD3^+$ T cells, and the methylation profile of GAPDH (AMP1570) were published previously (15).

Locus-specific relative qPCR measurements—To target differentially methylated CpG positions described above, discriminating qPCR assay systems were designed. These were characterized on synthetic template DNA cloned into plasmids. Templates correspond to the bisulfite modified genomic DNA, i.e., replacing all cytosines (C) with thymidines (T). For the TpG template (mimicking unmethylated CpGs), a universal plasmid carrying targets for all assays in an equimolar stoichiometry was designed. A universal CpG-plasmid (mimicking methylated CpGs) was generated accordingly. Exclusive amplification of the desired DNA sequence without cross-reactivity with mutually antithetic templates was demonstrated for all qPCRs (Table 1). Assay specificity was tested on immune cell populations, which were purified as described in the Materials and Methods section. For target cells, high copy numbers were observed in their respective TpG-specific system, and low copy numbers were measured in the corresponding CpG-system. Conversely, for control cells low and high copies were found in the TpG- and CpG-systems, respectively. The original copy number of the target gene was determined by relating qPCR signals from the according amplification (f) to amplification of serially diluted standard plasmids (f), each with a defined concentration of the in silico-converted unmethylated version. Relative determination of locus-specifically unmethylated DNA ($RD_{ls}$) ranged from 89.9 to 100% in target cell types and from 0 to 3% in controls (Table 1). Exceptions were observed for $CD4^+$ T cells, showing 8.9% $RD_{ls}$ at the CD8B locus and vice versa (i.e., 9.6% CD4 $RD_{ls}$ in $CD8^+$ T cells), possibly due to mutual and residual cell contaminations.

Universal and definitive quantification—Amplification efficiency and estimated copy numbers vary for each locus-specific qPCR system (25). Therefore, an invariably unmethylated regulatory region of the GAPDH (26) gene was used as a universal denominator to determine each cell-type locus relative to all nucleated cells. This system was applied to purified $CD3^+$, $CD4^+$ and $CD8^+$ T cells, neutrophils, $CD14^+$ monocytes, $CD56^+$ NK and $CD19^+$ B cells. Quantification differs when using methylated and unmethylated amplification data at specific epigenetic loci ($RD_{ls}$) compared with quantification of the unmethylated cell type-specific locus and the universally unmethylated GAPDH as the denominator ($RD_u$) (Table 1).

Figure 6:
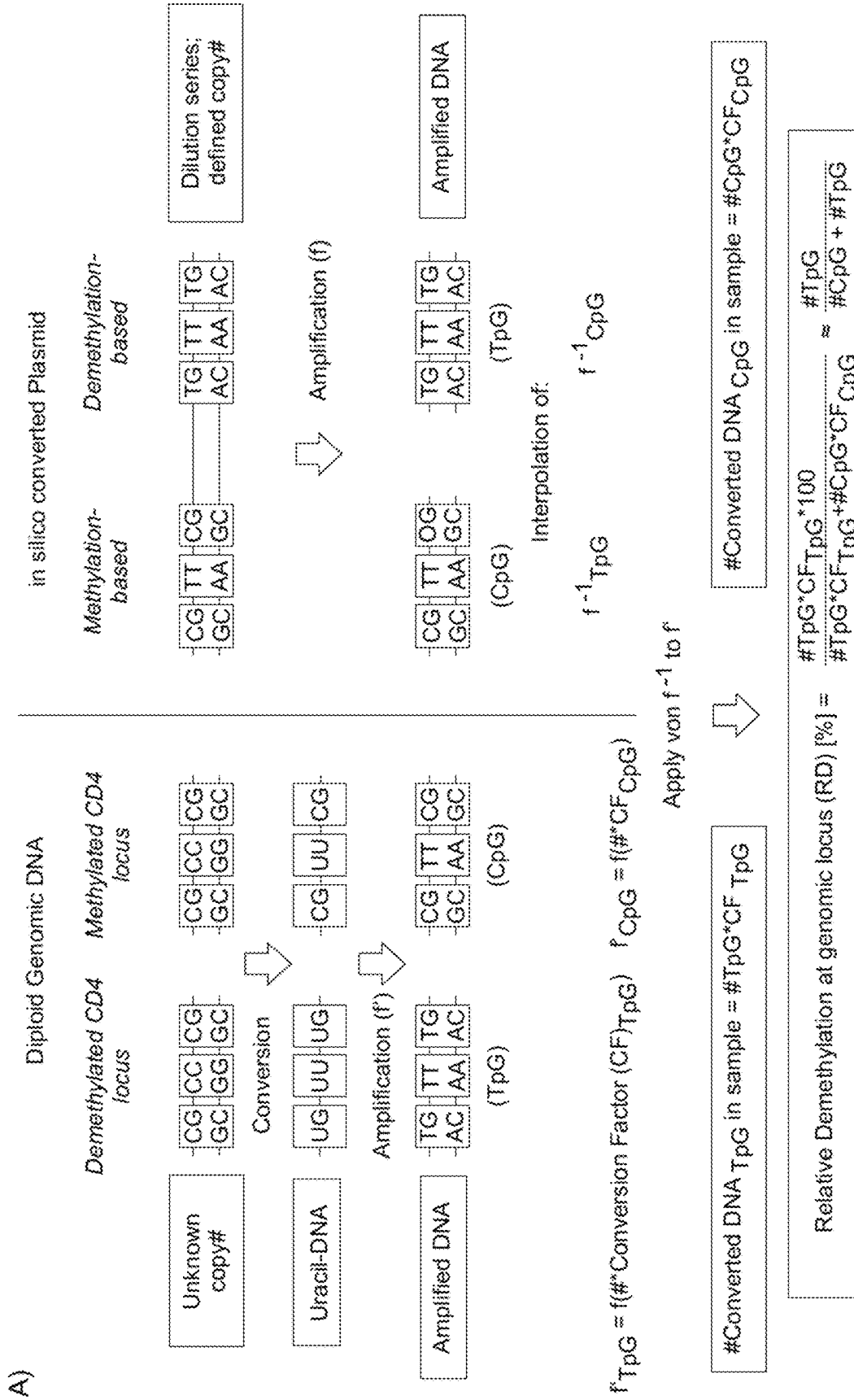
FIG. 6 shows a schematic overview over the different quantification approaches for epigenetic cell counting. In A) locus-specific relative percentage quantification is illustrated. qPCRs allow counting of copy numbers as based on the calculation of serially diluted in silico converted plasmids by a linear interpolation (f-1) of the amplification results (f). Relative percentage methylation at the genomic locus is calculated by the interpolated copy number of originally unmethylated copies at this locus divided by all copies at this locus, i.e., the methylated and unmethylated ones. Conversion in the biological sample perturbs the integrity of the genomic DNA, whereas the plasmid represents the amplification product and not the substrate. The resulting difference in amplification efficiency is given by an unknown "conversion factor, (CF)". It is considered negligible when comparing amplification of two highly homologous sequences with few methylation-status dependent SNPs. In (B) the universally unmethylated GAPDH locus (representing the total number of genomic DNA copies) is used as denominator to determine the ratio of any cell-type specifically unmethylated locus. Here, CF leads to substantial shifts between the different qPCR assays. In C) a calibrator plasmid containing equimolar genomic target sequences is used to compensate for conversion efficiencies at the different genomic loci introducing the efficiency factor (EF). D) For counting absolute numbers of cells in a defined volume of blood, a known copy number of plasmid containing a synthetic, not natural DNA sequence (GAP-GC) is supplemented. Interpolating the starting amount of GAP-GC allows monitoring of DNA preparation, conversion and qPCR providing a good estimator for process efficacy.
Figure 6:
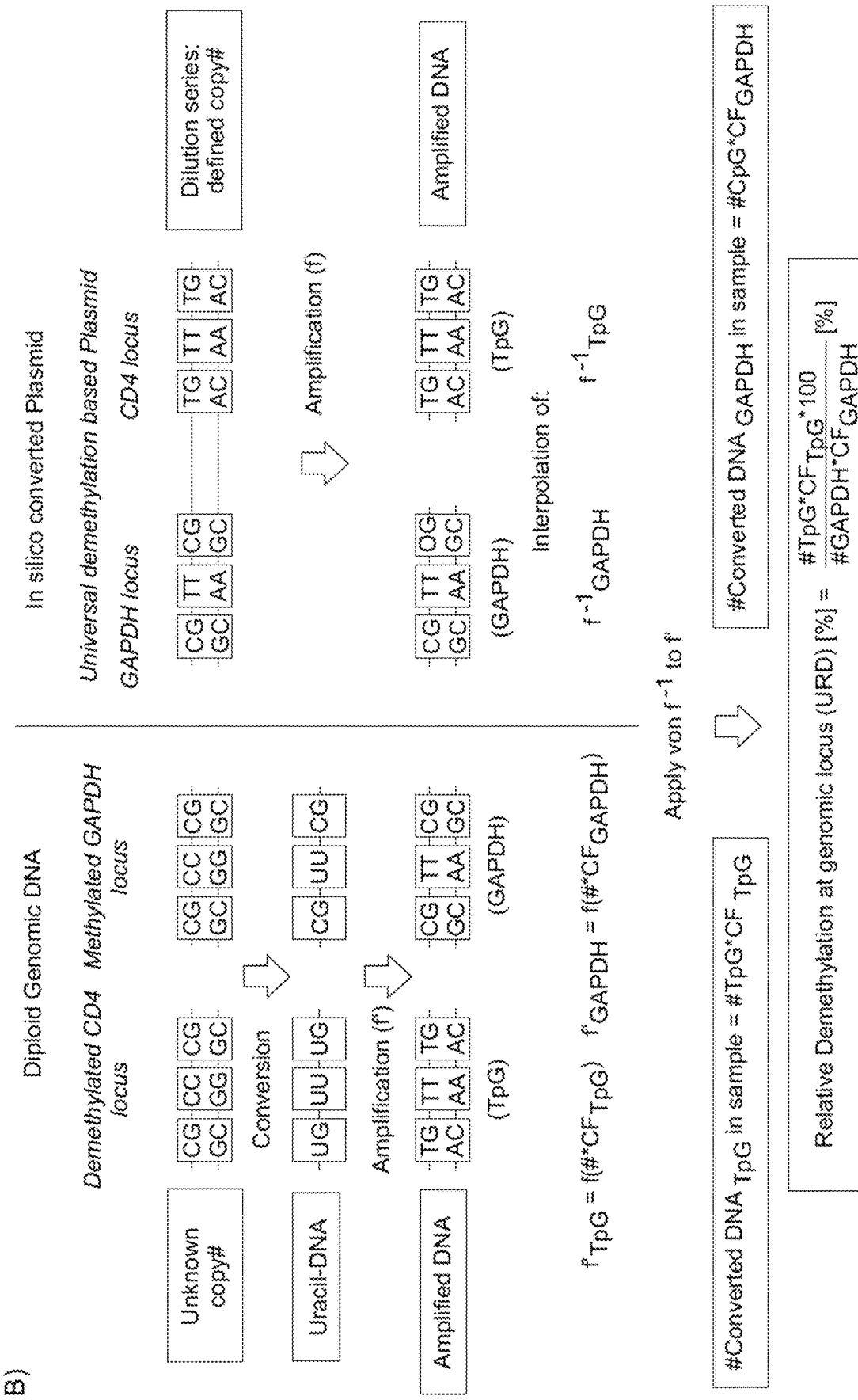
Figure 6:
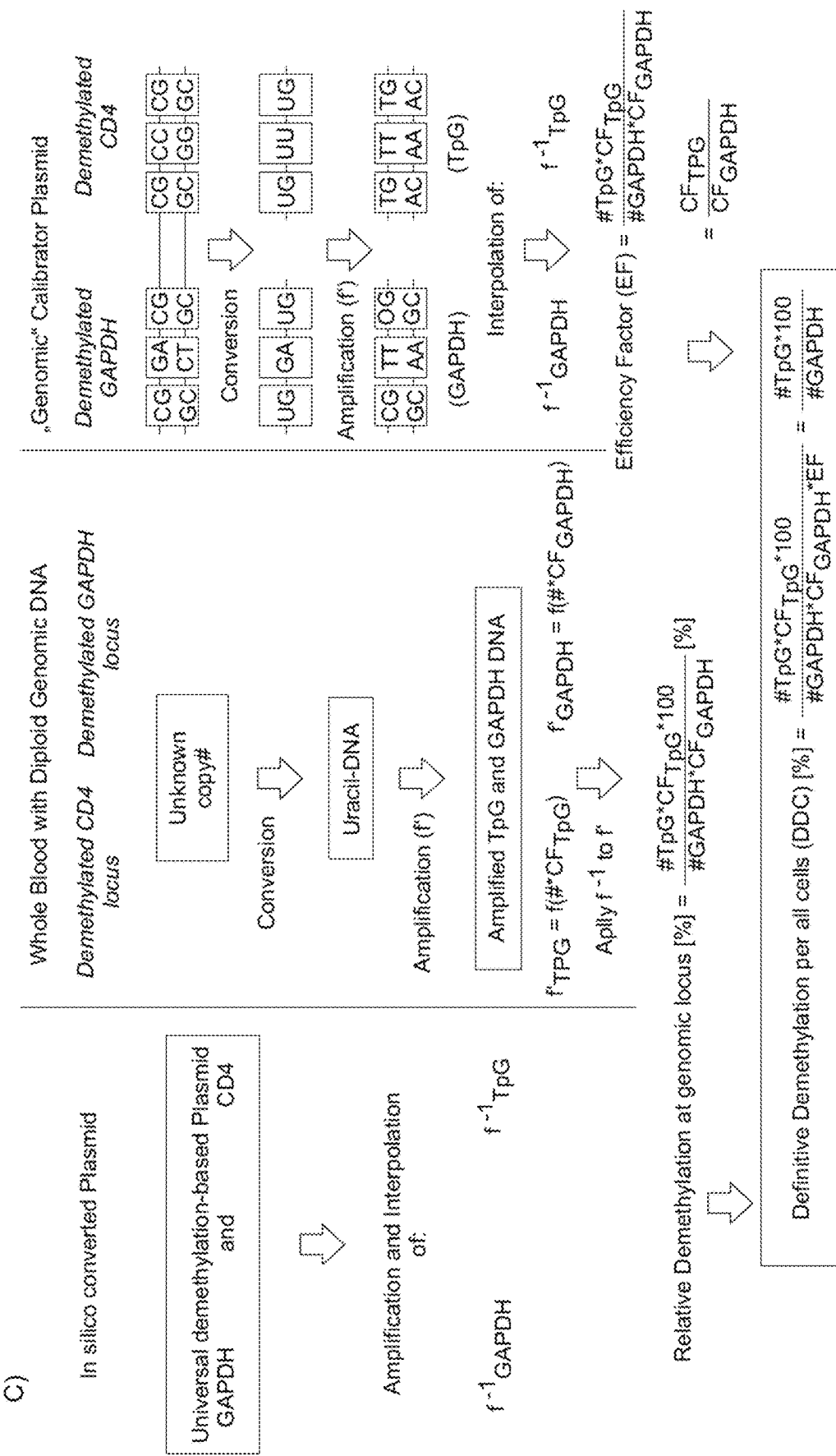
Figure 6:
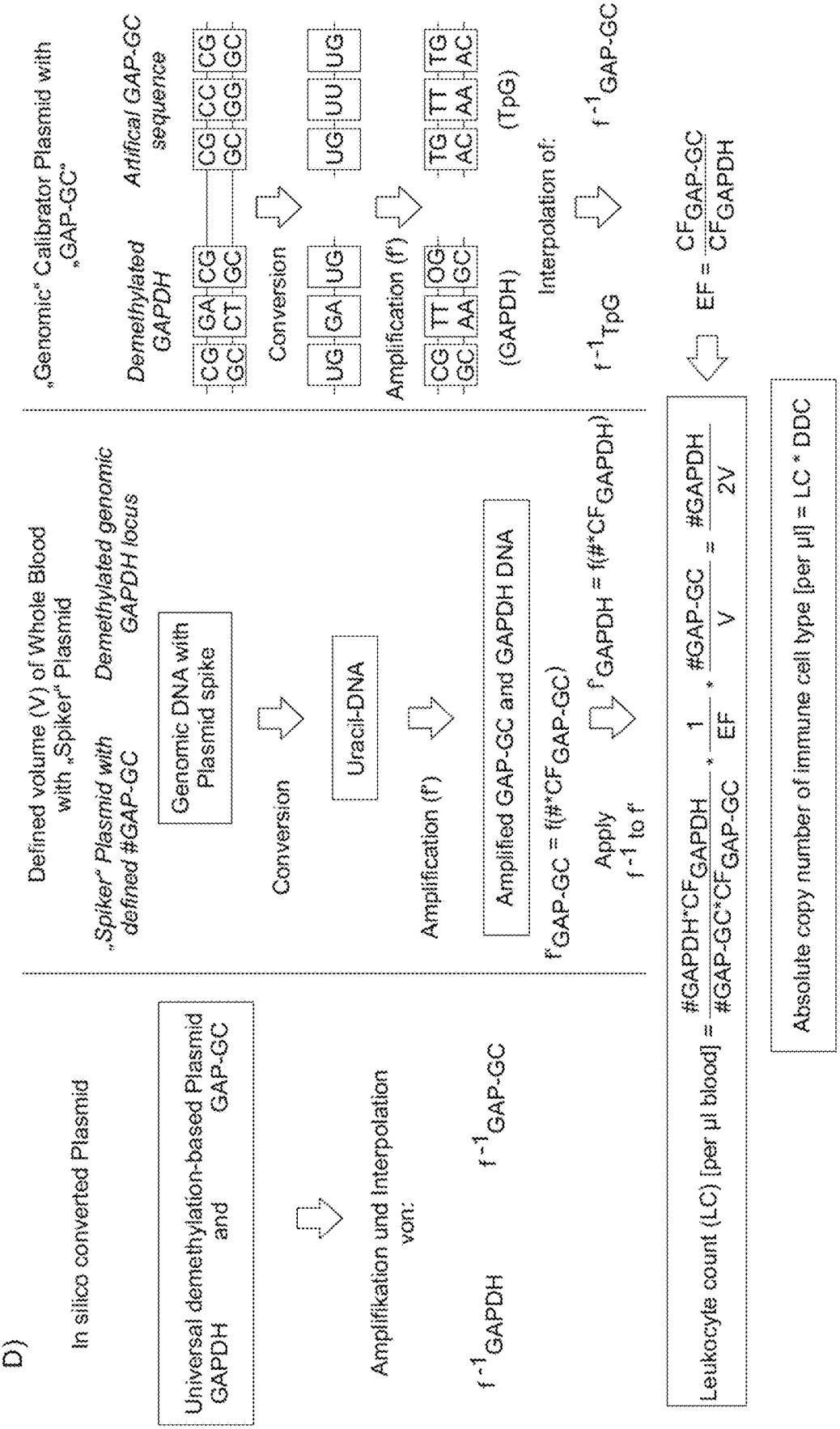

Since in silico-converted double-stranded, GC-rich plasmids do not fully represent de facto bisulfite-converted, single-stranded GC-depleted DNA (27, 28), a "calibrator plasmid" was adopted harboring one copy of all assay targets in their unconverted genomic (i.e., unmethylated) state. This calibrator is bisulfite-converted in parallel to samples. When copy numbers from this calibrator are obtained by standard plasmid interpolation, systematic amplification differences between the assays were detected and translated into an efficiency factor (EF), adjusting for biases between cell-type specific assays and GAPDH. Cell type-specific EFs were measured in approximately 25 experiments ranging between 0.53 (95% confidence interval (CI)=0.42, 0.61) for CD4 and 1.17 (95% CI=0.95, 1.31) for CD3D/G (see "Epigenetic qPCR" in Material and Method Section). Calculated EFs provide universal definitive determination of unmethylated DNA ($DD_u$) for each assay (Table 1). Using this approach, the inventors applied epigenetic qPCR for universal and definitive quantification of immune cells from biological samples. The concepts of immune cell quantification used in this work are illustrated in FIG. 6.

Method comparison of FCM and epigenetic qPCR—To allow absolute cell quantification comparable to FCM (i.e., cell/μl) the inventors introduced a "spike-in plasmid" harboring an artificial GAPDH-derived sequence, created by inversing all CpG dinucleotides to GpC (GAP[GC]) and an according epigenetic qPCR. For absolute immune cell counting, this plasmid was added to blood samples in a defined concentration. The in silico bisulfite-converted, artificial GAP[GC] sequence was included in the quantification standard and the unconverted sequence into the calibrator plasmid.

Figure 2:
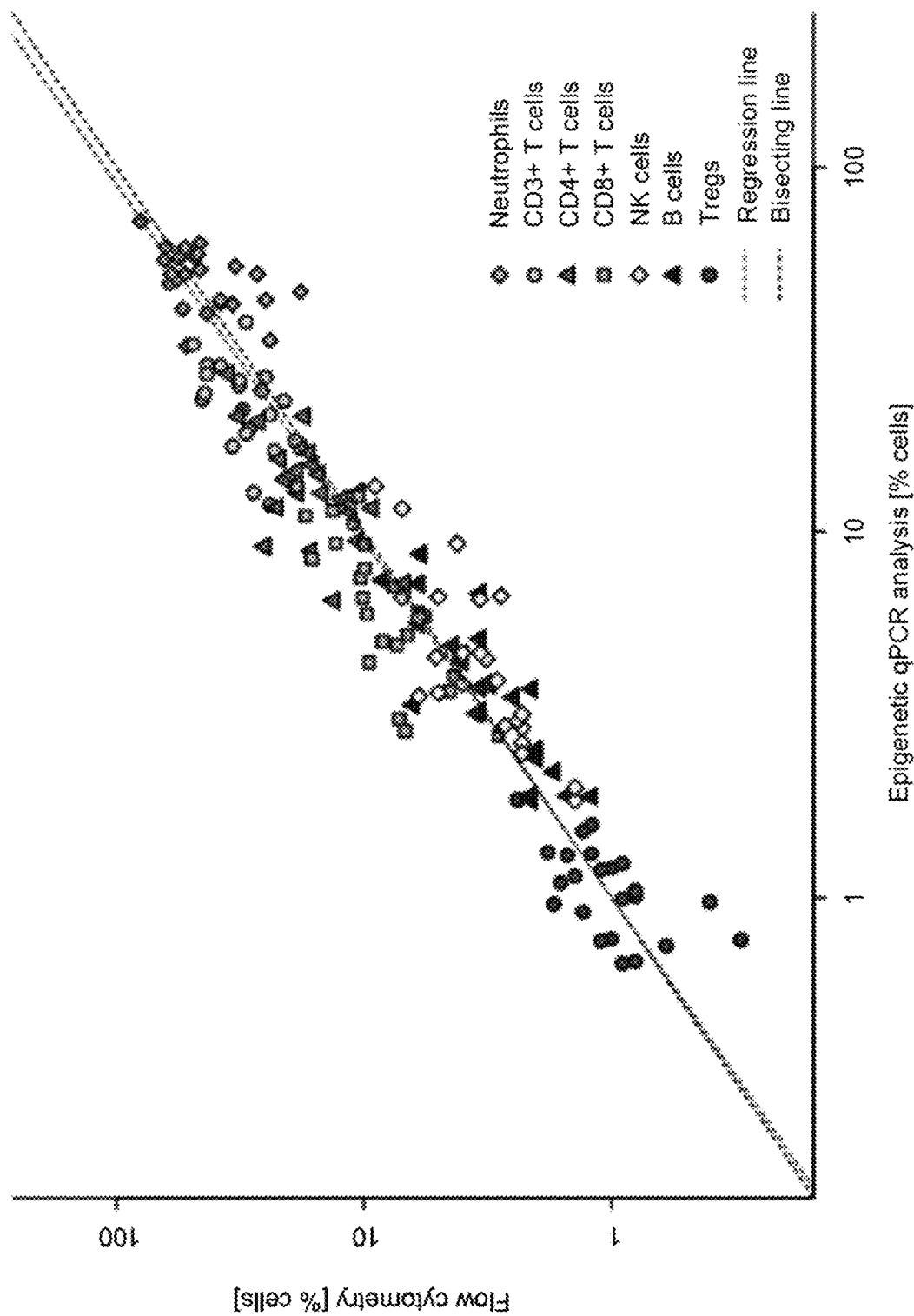
FIG. 2 shows a comparison of immune cell quantification by FCM and epigenetic qPCR. Immune cells from 25 blood samples of independent donors were measured with flow cytometry (y-axis) and epigenetic qPCR (x-axis). In A) relative immune cell counts are shown as percent of total leukocytes. In B) absolute immune cell counts are shown as cell number per µl whole blood. The regression line is depicted as computed from all data points, the bisectrix is also shown.
Figure 2:
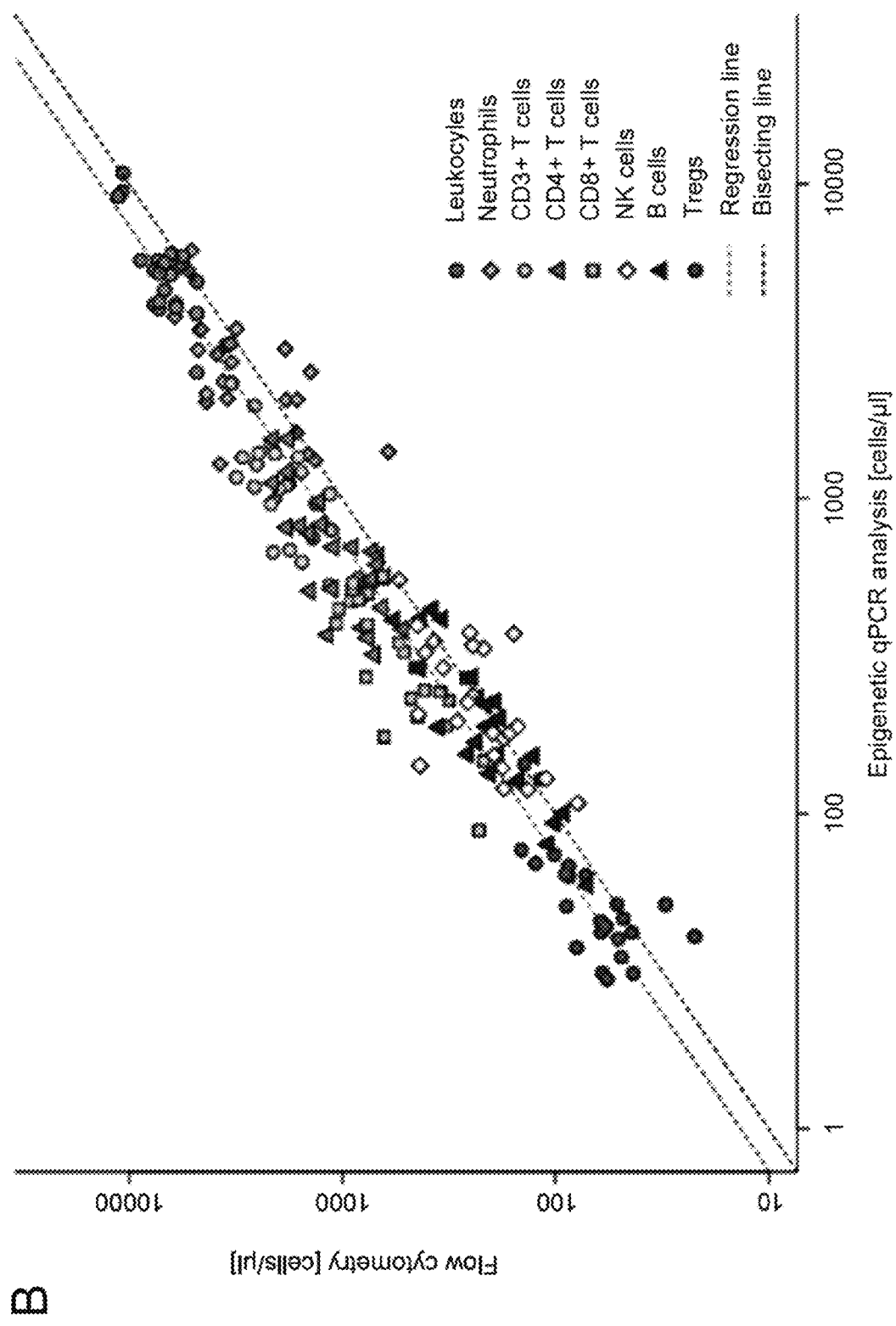

To assess the overall performance of the epigenetic cell counting, markers for B cells, NK cells, $CD3^+$, $CD4^+$, $CD8^+$ T cells, $FOXP3^+$ Tregs and neutrophils were analyzed in blood samples from 25 adult healthy donors in comparison with FCM. Data from both methods were scatter plotted either as relative (FIG. 2A) or absolute cell counts (FIG. 2B), each yielding Pearson coefficients (r) of above 0.95 (p<0.0001).

Figure 3:
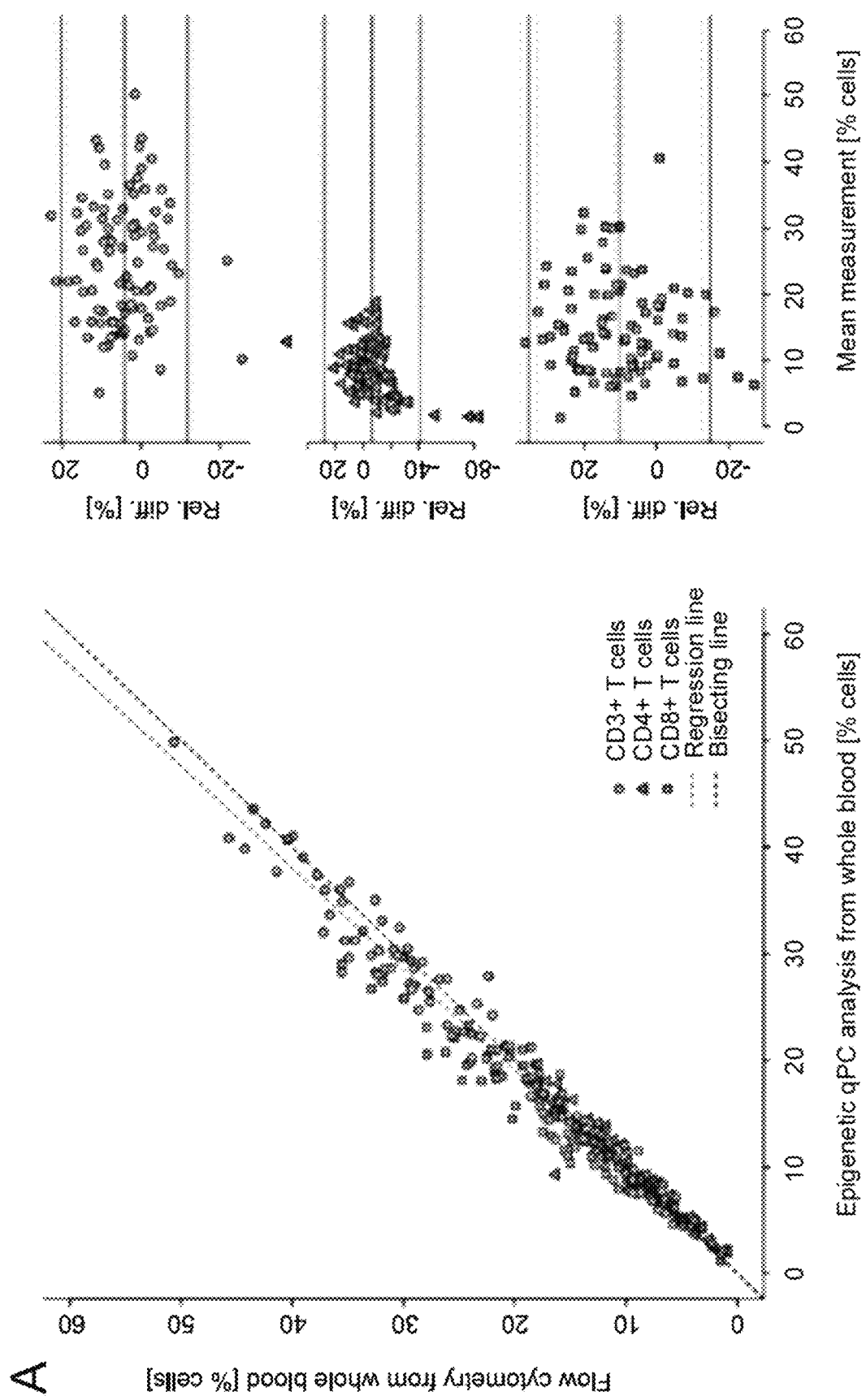
FIG. 3 shows the method comparison of T cell subsets in a HIV cohort. Relative counts of $CD3^+$, $CD4^+$ and $CD8^+$ T cells in % of total nucleated cells determined by (A) FCM and epigenetic qPCR in liquid whole blood, (B) FCM as in A) and epigenetic qPCR from DBS, and (C) comparison of epigenetic qPCR from liquid blood and DBS. On the lefthand side, data are presented as scatterplots. The regression line is depicted as computed from all data points, the bisectrix is also shown. On the righthand side Bland-Altman plots show average cell counting of the respective analyses (x-axis) plotted over their relative difference (y-axis). Lines reflect limits of agreement. Central lines illustrate the systematic bias. The respective 95% CIs are shown as dotted lines. Upper panel: Total $CD3^+$ T cells; Middle panel: $CD4^+$ T cells; bottom right: $CD8^+$ T cells.
Figure 3:
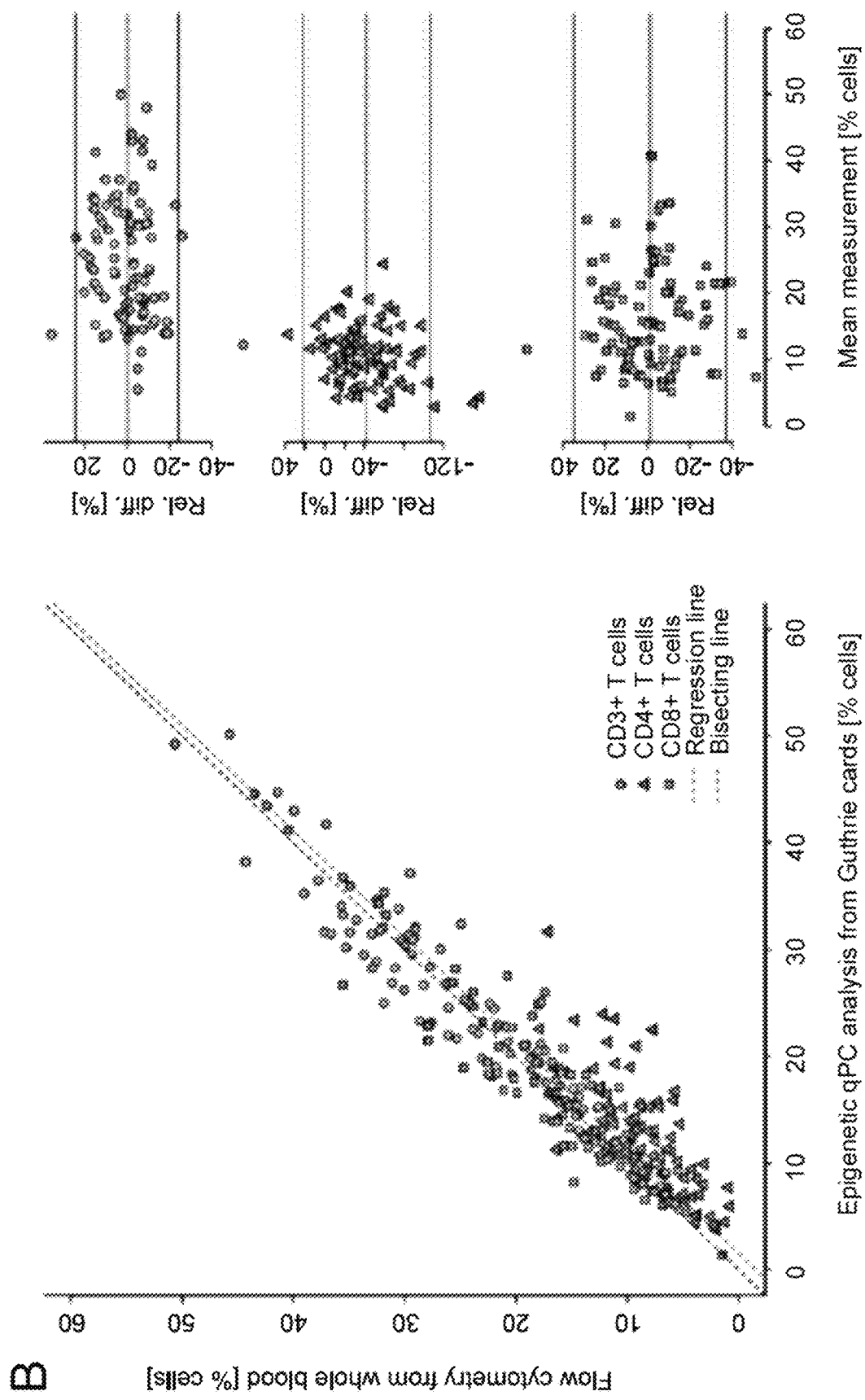
Figure 3:
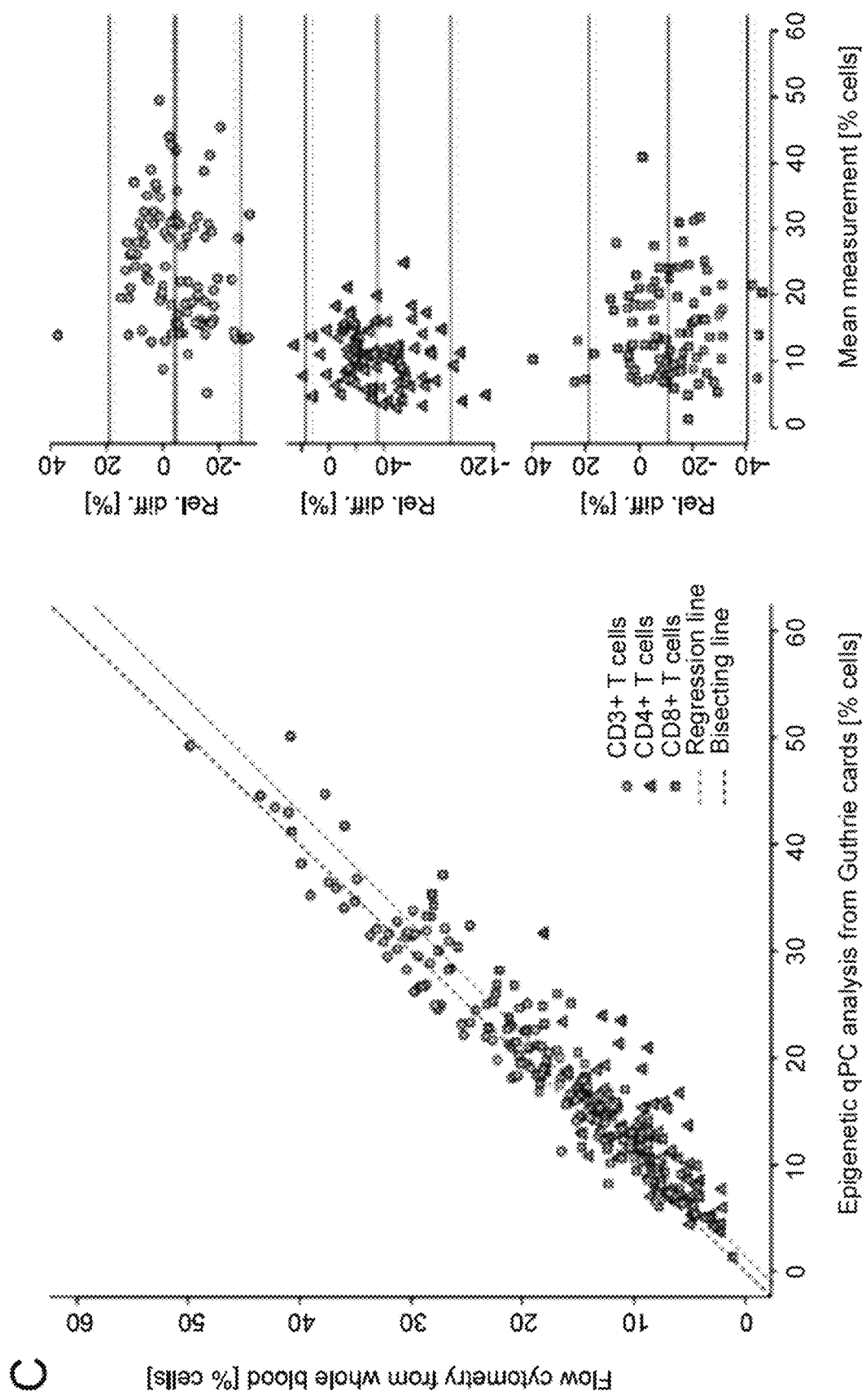
Figure 7:
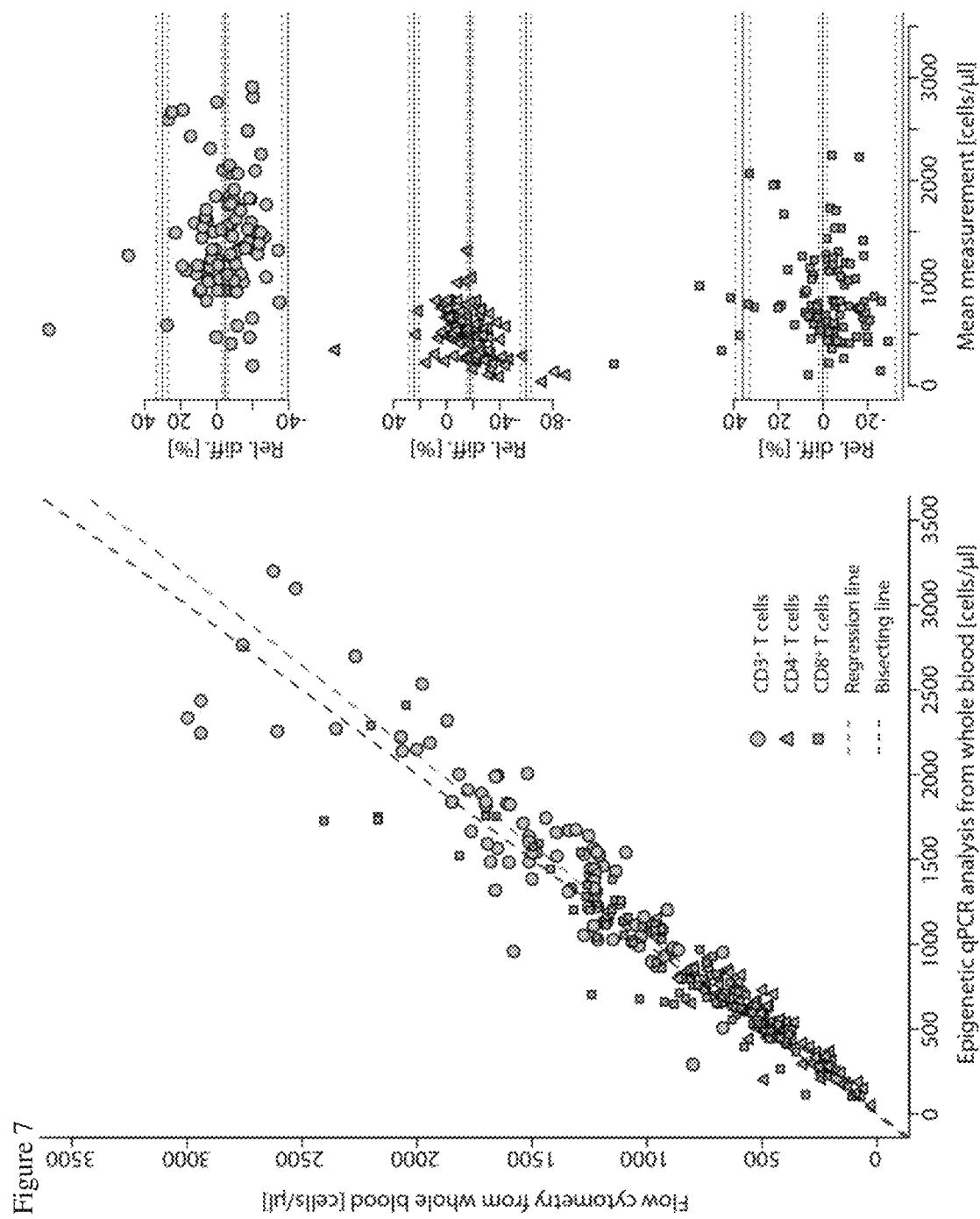
FIG. 7 shows a correlation analysis of absolute quantification for T cell subsets in a HIV cohort. Absolute immune cell counts (as expressed in cells per μl blood) were measured from blood samples of 97 HIV$^+$ patients by means of flow cytometry and epigenetic qPCR analysis. The graph at the left side scatter plots three T cell populations as measured by epigenetic qPCR analysis (x-axis) and flow cytometry (y-axis). The lines represent the bisectrix and the regression line. Pearson correlation coefficient r=0.955 (p<0.0001). The graphs on the right side display a Bland-Altman plot with the mean cell count (cells per μl) averaged between each epigenetic and cytometric measurement on the x-axis plotted over their (relative) difference (y-axis). Lines reflect the limits of concordance and the central line illustrates the systematic bias. Above and below each of these lines, the respective 95% confidence intervals are shown as dotted lines. Upper panel: Total CD3$^+$ T cells; middle panel: CD8$^+$ T cells; bottom right: CD4$^+$ T cells.
Figure 8:
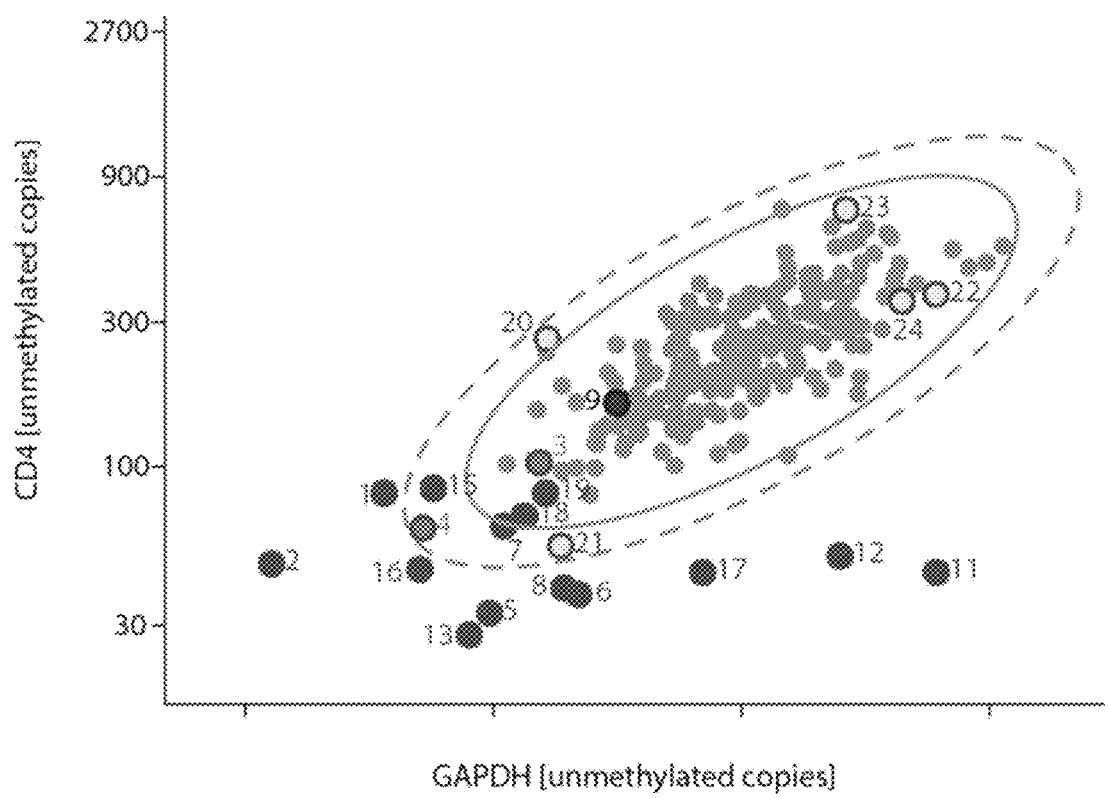
FIG. 8 shows epigenetic immune cell quantification on DBS from newborns. Dried blood spots on Guthrie cards were subjected to epigenetic qPCR analysis for the quantification of unmethylated CD4 (A; specific for CD4$^+$ T cells) and CD8B (B, specific for CD8B$^+$ T cells) gene copies. Calculated values from the immune cell specific assays (y-axis) were scatter plotted over parallel measured GAPDH copies (x-axis). Reference samples from healthy neonates (n=250, clustered dots) were measured and used to estimate normal ranges for each assay as defined by inner (99% confidence region) and outer (99.9% confidence region) ellipses, respectively. 24 samples from newborns each with a diagnosed PID (classification as indicated in the legend box) are shown as numbered circles, each associated with an identifier referencing disease characteristics according to Table 2.
Figure 8:
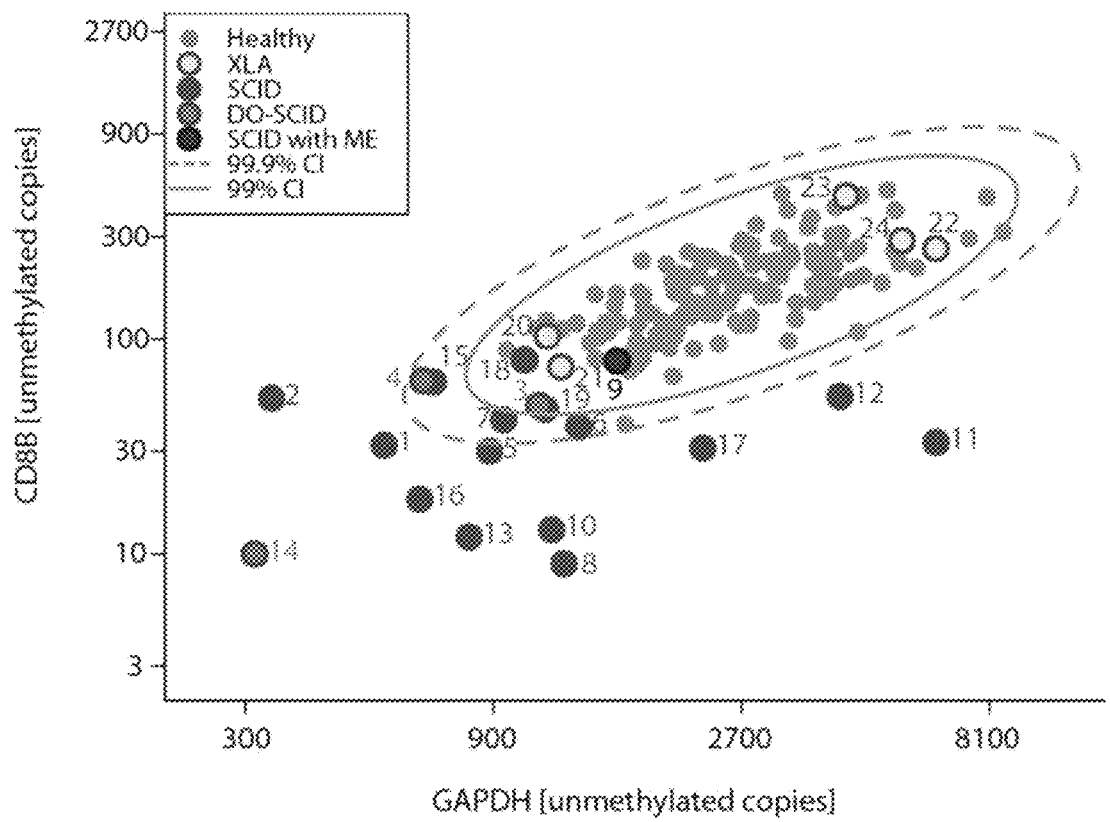

To test the individual epigenetic markers in a clinically relevant setting, the inventors used blood from 97 $HIV^+$ subjects and quantified $CD3^+$, $CD4^+$ and $CD8^+$ T cell counts by standard FCM and epigenetic qPCR. For the latter, EDTA-blood or DBS served as substrates. Method comparisons were conducted for all three approaches. For comparison of FCM to epigenetic qPCR in liquid blood, correlation analyses yielded Pearson r coefficients from 0.96 to 0.98 (p<0.001) for relative quantification (FIG. 3A). Leukocyte numbers per microliter blood as determined by FCM and epigenetic qPCR were highly correlated (Pearson r=0.8; p<0.001) (FIG. 7). Comparative analyses from DBS and FCM (FIG. 3B) yielded Pearson r between 0.7 and 0.95 (p<0.001). Epigenetic measurements from liquid blood and DBS yielded Pearson r between 0.8 and 0.95 (p<0.001) (FIG. 3C).

Bland-Altman analyses ((29) shown in FIG. 3A-C, (right panels) determines systematic biases and precision for all methods and markers which are listed in Table 6. Biological read-outs of FCM and epigenetic counting from either substrate correlated well for the tested cell types. Minor biases (4.3-; -6.6; 10.3 for CD3, CD4, CD8, respectively) and high precision (all <20%) were detected between FCM and epigenetic qPCR of liquid blood whereas a pronounced variation (>20%) was observed between DBS and both other methods for $CD4^+$ T cells. To investigate the influence of substrate instability in DBS, different storage times and conditions and sample dilutions, mimicking unobservantly collected DBS, were monitored. Data showed no sign of degradation at different storage conditions with change of variation (CV) below 15% for all temperatures and time points (Table 5). CV was below 30% down to blood dilutions of 1:9 (Table 6). As previously analyzed by others, genomic DNA is a stable analyte and can be extracted from year-long stored DBS (30-32).

Figure 4:
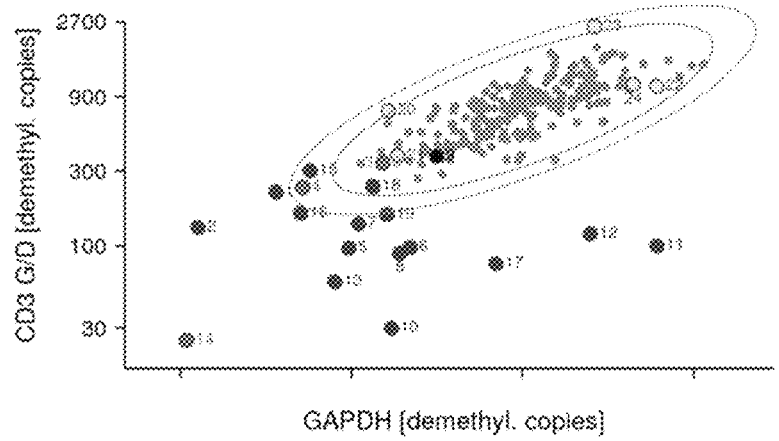
FIG. 4 shows the epigenetic qPCR of neonatal DBS. Copies from cell-type specific qPCRs (y-axis) plotted against GAPDH copies (x-axis). (A) unmethylated CD3G/D, B) MVD and C) LRP5. DBS from healthy neonates (n=250, clustered circles) estimate reference ranges for each assay as defined by 99% confidence region (inner ellipse) and 99.9% confidence region (outer ellipse). 24 DBS from PID-diagnosed newborns are shown as numbered circles, each referencing disease characteristics shown in Table 2.
Figure 4:
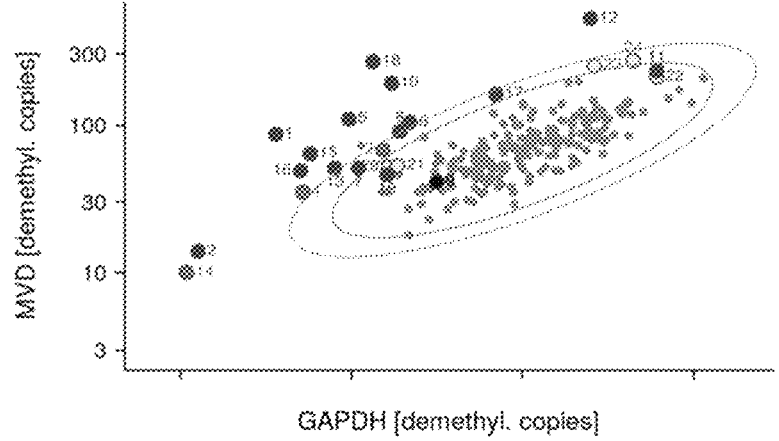
Figure 4:
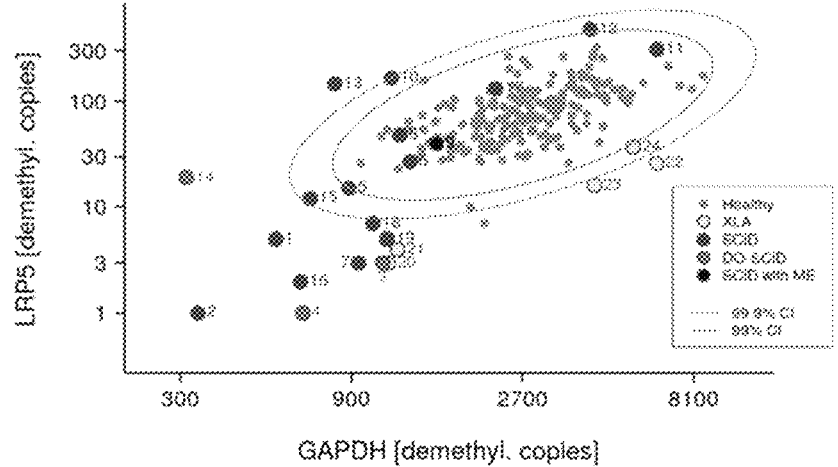

Epigenetic qPCR in neonatal screening samples—Epigenetic qPCR was applied in a case/control study consisting of original neonatal screening cards (i.e., DBS) from 24 PID patients and 250 randomly selected newborns, measuring total T, B and NK cells (FIG. 4). PID cases included SCID patients with different gene defects and X-linked agammaglobulinemia (XLA) associated with BTK-mutation (Table 2). Reference ranges were established using the joint distribution of all leukocytes (GAPDH-specific qPCR) and specific immune cell types. Copy numbers were log-transformed and used to estimate a bivariate normal distribution, whose confidence regions (99% and 99.9% curves) defined reference ranges for newborns. As each of the three panels is tuned to 99% or 99.9% confidence regions, Bonferroni correction guarantees family-wise-error-rates below 3% or 0.3% yielding final confidence of 99.7 or 97%, respectively.

For $CD3^+$ T cell- and GAPDH-measurements, 13 out of 16 samples from SCID patients were outside the 99.9% confidence region, SCID15 was found outside the 99%, but inside the 99.9% region and SCID9 and 18 presented as non-suspicious. However, SCID15 and 18 were outside the 99.9% confidence region for NK cell and GAPDH measurements. Moreover, for B cell and GAPDH measurements, SCTD18 was found outside the 99.9% confidence region and SCID15 was found outside the 99% region (FIG. 4). Hence, 15 out of 16 SCID patients were unambiguously identified as non-normal by epigenetic testing based on their newborn cards. SCID9 presented with maternal lymphocyte engraftment, as confirmed by FCM and chromosomal analysis, did however not show a quantitative impairment of cell counts and is classified as normal. Epigenetic qPCR for $CD4^+$, $CD8^+$ T cells and GAPDH confirmed these findings without adding diagnostic information to $CD3^+$ T cell analysis in SCID samples. DBS of delayed-onset SCID (DO-SCID) associated with hypomorphic JAK3 or ADA mutations were also analyzed. The JAK3 deficient delayed-onset patient (DO-SCID14) showed reduced CD3, NK, B and CD4, CD8 values (FIG. 4) outside the 99.9% confidence region. ADA-associated DO-SCID4 was outside the 99.9% confidence region for NK and B cells and outside the 99% region for CD3, whereas DO-SCID3 was outside the 99.9% confidence region in B cells and the 99% confidence region in NK but normal for $CD3^+$ T cells. Overall, all three DO-SCID samples were identified based on epigenetic analysis. DBS from four out of five patients with XLA showed B cell counts outside of the 99.9% confidence region. Hypomorphic XLA24 was outside the 99% confidence region in B and NK cells. NK and T cell counts were at the borders of reference ranges for other XLA samples (XLA23 in NK and XLA20, XLA23 in Tcells). Altogether the XLA phenotype was in accordance with B cell deficiency. Comparison with TREC/KREC values showed that epigenetic quantification detected all but one patient, whereas TREC/KREC failed to detect two of five cases with delayed-onset or hypomorphic genetic background. However, maternal engraftment masks detection via epigenetic counting, whereas TREC analysis is not affected (Table 2). Screening classification is based on the three tests for conspicuous cell counts attains a sensitivity of 0.958 and a specificity of 0.984 using the 99% confidence regions. For the 99.9% confidence regions, sensitivity falls to 0.9167, while the specificity reaches 1.

IPEX and severe congenital neutropenias (SCN) are other forms of severe PID with no currently available newborn screening. Given their severe early-onset and morbidity, patients would benefit from neonatal diagnosis. In juvenile IPEX patients peripheral Tregs are uniquely increased (23), when compared to healthy age-matched donors and disease controls.

Applying epigenetic qPCR for neutrophils, neonatal patients with SCN were detected by a significant reduction (p=4.4×10e−6) of neutrophils (FIG. 5A). The median percentage of neutrophils was at 55% in the control cards (n=26) and at 17% in neutropenic patients (n=6). Tested was a DBS each from a newborn and a two-year old IPEX patient by epigenetic qPCR of Treg and $CD3^+$ T cells (FIG. 5B). The ratio of Treg/$CD3^+$ T cells of IPEX patients is conspicuously increased compared to the non-affected healthy donors.

REFERENCES AS CITED

1. A. Adan, G. Alizada, Y. Kiraz, Y. Baran, A. Nalbant, Flow cytometry: basic principles and applications, *Crit. Rev. Biotechnol.* 8551, 1-14 (2016).
2. L. Whitby, A. Whitby, M. Fletcher, D. Barnett, Current laboratory practices in flow cytometry for the enumeration of CD 4+T-lymphocyte subsets *Cytom. Part B-Clin. Cytom.* 88, 305-311 (2015).
3. C. T. Nebe, A. Dorn-Beineke, P. Braun, V. Daniel, Z. Ilieva, G. Kuling, C. Meisel, U. Oelschlägel, U. Sack, Messunsicherheit und Qualitätssicherung im Bereich der Immunphänotypisierung der Lymphozytensubpopulationen im peripheren Blut *LaboratoriumsMedizin* 37, 233-250 (2013).
4. L. A. Herzenberg, J. Tung, W. A. Moore, L. A. Herzenberg, D. R. Parks, Interpreting flow cytometry data: A guide for the perplexed *Nat. Immunol.* 7, 681-685 (2006).
5. A. H. Kverneland, M. Streitz, E. Geissler, J. Hutchinson, K. Vogt, D. Boës, N. Niemann, A. E. Pedersen, S. Schlickeiser, B. Sawitzki, Age and gender leucocytes variances and references values generated using the standardized ONE-Study protocol, *Cytom. Part A* 89, 543-564 (2016).
6. H. T. Maecker, J. P. McCoy, R. Nussenblatt, Standardizing immunophenotyping for the Human Immunology Project *Nat. Rev. Immunol.* 12, 191-200 (2012).
7. H. T. Maecker, J. P. McCoy, M. Amos, J. Elliott, A. Gaigalas, L. Wang, R. Aranda, J. Banchereau, C. Boshoff, J. Braun, Y. Korin, E. Reed, J. Cho, D. Hafler, M. Davis, C. G. Fathman, W. Robinson, T. Denny, K. Weinhold, B. Desai, B. Diamond, P. Gregersen, P. Dimeglio, F. Nestle, M. Peakman, F. Villnova, J. Ferbas, E. Field, A. Kantor, T. Kawabata, W. Komocsar, M. Lotze, J. Nepom, H. Ochs, R. O'Lone, D. Phippard, S. Plevy, S. Rich, M. Roederer, D. Rotrosen, J. H. Yeh, A model for harmonizing flow cytometry in clinical trials *Nat. Immunol.* 11, 975-978 (2010).
8. World Health Organization, Consolidated guidelines on the use of antiretroviral drugs for treating and preventing HIV infection: recommendations for a public health approach, *World Heal. Organ.,* 155 p. (2016).
9. L. Ryom, C. Boesecke, V. Gisler, C. Manzardo, J. K. Rockstroh, M. Puoti, H. Furrer, J. M. Miro, J. M. Gatell, A. Pozniak, G. Behrens, M. Battegay, J. D. Lundgren, C. Manzardo, A. d. A. Monforte, J. Arribas, N. Clumeck, N. Dedes, A. M. Geretti, A. Horban, C. Katlama, S. McCormack, J. M. Molina, C. Mussini, F. Raffi, P. Reiss, H. J. Stellbrink, G. Behrens, M. Bower, P. Cinque, S. Collins, J. Compston, G. Deray, S. De Wit, C. A. Fux, G. Guraldi, P. Mallon, E. Martinez, C. Marzolini, S. Papapoulos, R. du Pasquier, N. Poulter, I Williams, A. Winston, M. Puoti, S. Bhagani, R. Bruno, S. Konov, K. Lacombe, S. Mauss, L. Mendao, L. Peters, A. Rauch, C. Tural, H. Furrer, J. M. Miro, V. Gisler, G. Fätkenheuer, O. Kirk, A. Mocroft, P. Morlat, A. Volny-Anne, F. Mulcahy, C. Katlama, C. Oprea, M. Youle, Essentials from the 2015 European AIDS Clinical Society (EACS) guidelines for the treatment of adult HIV-positive persons, *HIV Med.* 17, 83-88 (2016).
10. J. van der Spek, R. H. H. Groenwold, M. van der Burg, J. M. van Montfrans, TREC Based Newborn Screening for Severe Combined Immunodeficiency Disease: A Systematic Review, *J. Clin. Immunol.* 35, 416-430 (2015).
11. A. Sottini, C. Ghidini, C. Zanotti, M. Chiarini, L. Caimi, A. Lanfranchi, D. Moratto, F. Porta, L. Imberti, Simultaneous quantification of recent thymic T-cell and bone marrow B-cell emigrants in patients with primary immunodeficiency undergone to stem cell transplantation, *Clin. Immunol.* 136, 217-227 (2010).
12. J. King, J. Ludvigsson, L. Hammarström, Newborn Screening for Primary Immunodeficiency Diseases: The Past, the Present and the Future, *Int. J. Neonatal Screen.* 3, 19 (2017).
13. U. Baron, S. Floess, G. Wieczorek, K. Baumann, A. Grützkau, J. Dong, A. Thiel, T. J. Boeld, P. Hoffmann, M. Edinger, I. Türbachova, A. Hamann, S. Olek, J. Huehn, DNA demethylation in the human FOXP3 locus discriminates regulatory T cells from activated FOXP3+ conventional T cells, *Eur. J. Immunol.* 37, 2378-2389 (2007).
14. G. Wieczorek, A. Asemissen, F. Model, I. Turbachova, S. Floess, V. Liebenberg, U. Baron, D. Stauch, K. Kotsch, J. Pratschke, A. Hamann, C. Loddenkemper, H. Stein, H. D. Volk, U. Hoffmller, A. Grutzkau, A. Mustea, J. Huehn, C. Scheibenbogen, S. Olek, Quantitative DNA methylation analysis of FOXP3 as a new method for counting regulatory T cells in peripheral blood and solid tissue, *Cancer Res.* 69, 599-608 (2009).
15. J. Sehouli, C. Loddenkemper, T. Cornu, T. Schwachula, U. Hoffmüller, A. Gr??tzkau, P. Lohneis, T. Dickhaus, J. Gr??ne, M. Kruschewski, A. Mustea, I. Turbachova, U. Baron, S. Olek, Epigenetic quantification of tumor-infiltrating T-lymphocytes, *Epigenetics* 6, 236-246 (2011).
16. S. Rapko, U. Baron, U. Hoffmüller, F. Model, L. Wolfe, S. Olek, DNA methylation analysis as novel tool for quality control in regenerative medicine, *Tissue Eng.* 13, 2271-80 (2007).
17. T. O. Kleen, J. Yuan, Quantitative real-time PCR assisted cell counting (qPACC) for epigenetic—based immune cell quantification in blood and tissue, *J. Immunother. Cancer* 3 (2015), doi:10.1186/s40425-015-0087-8.
18. E. A. Houseman, W. P. Accomando, D. C. Koestler, B. C. Christensen, C. J. Marsit, H. H. Nelson, J. K. Wiencke, K. T. Kelsey, DNA methylation arrays as surrogate measures of cell mixture distribution, *BMC Bioinformatics* 13 (2012), doi:10.1186/1471-2105-13-86.
19. W. P. Accomando, J. K. Wiencke, E. A. Houseman, H. H. Nelson, K. T. Kelsey, Quantitative reconstruction of leukocyte subsets using DNA methylation, *Genome Biol.* 15 (2014), doi:10.1186/gb-2014-15-3-r50.
20. J. W. Lee, V. Devanarayan, Y. C. Barrett, R. Weiner, J. Allinson, S. Fountain, S. Keller, I. Weinryb, M. Green, L. Duan, J. A. Rogers, R. Millham, P. J. O'Brien, J. Sailstad, 20. M. Khan, C. Ray, J. A. Wagner, in *Pharmaceutical Research*, (2006), vol. 23, pp. 312-328.
21. P. Kung, G. Goldstein, E. L. Reinherz, S. F. Schlossman, Monoclonal antibodies defining distinctive human T cell surface antigens, *Science* (80-.). 206, 347-9 (1979).
22. R. E. L., S. S. F., Regulation of the Immune Response—Inducer and Suppressor T-Lymphocyte Subsets in Human Beings, *N. Engl. J Med.* 303, 370-373 (1980).
23. F. Barzaghi, L. Passerini, E. Gambineri, S. Ciullini Mannurita, T. Cornu, E. S. Kang, Y. H. Choe, C. Cancrini, S. Corrente, R. Ciccocioppo, M. Cecconi, G. Zuin, V. Discepolo, C. Sartirana, J. Schmidtko, A. Ikinciogullari, A. Ambrosi, M. G. Roncarolo, S. Olek, R. Bacchetta, Demethylation analysis of the FOXP3 locus shows quantitative defects of regulatory T cells in IPEX-like syndrome, *J. Autoimmun.* 38, 49-58 (2012).
24. J. Lewin, A. O. Schmitt, P. Adorján, T. Hildmann, C. Piepenbrock, Quantitative DNA methylation analysis based on four-dye trace data from direct sequencing of PCR amplificates, *Bioinformatics* 20, 3005-3012 (2004).
25. P. M. Warnecke, C. Stirzaker, J. R. Melki, D. S. Millar, C. L. Paul, S. J. Clark, Detection and measurement of PCR bias in quantitative methylation analysis of bisulphite-treated DNA, *Nucleic Acids Res.* 25, 4422-4426 (1997).
26. H. J. M. de Jonge, R. S. N. Fehrmann, E. S. J. M. de Bont, R. M. W. Hofstra, F. Gerbens, W. A. Kamps, E. G. E. de Vries, A. G. J. van der Zee, G. J. te Meerman, A. ter Elst, Evidence Based Selection of Housekeeping Genes, *PLoS One* 2, e898 (2007).
27. D. Chen, P. S. Rudland, H. L. Chen, R. Barraclough, Differential reactivity of the rat S100A4(p9Ka) gene to sodium bisulfite is associated with differential levels of the S100A4 (p9Ka) mRNA in rat mammary epithelial cells, *J. Biol. Chem.* 274, 2483-2491 (1999).
28. J. Harrison, C. Stirzaker, S. J. Clark, Cytosines adjacent to methylated CpG sites can be partially resistant to conversion in genomic bisulfite sequencing leading to methylation artifacts *Anal. Biochem.* 264, 129-132 (1998).
29. D. Giavarina, Understanding Bland Altman analysis, *Biochem. Medica* 25, 141-151 (2015).
30. S. Chaisomchit, R. Wichajarn, N. Janejai, W. Chareonsiriwatana, Stability of genomic DNA in dried blood spots stored on filter paper, *Southeast Asian J. Trop. Med. Public Health* 36, 270-273 (2005).
31. M. V. Hollegaard, J. Grauholm, B. Norgaard-Pedersen, D. M. Hougaard, DNA methylome profiling using neonatal dried blood spot samples: A proof-of-principle study, *Mol. Genet. Metab.* 108, 225-231 (2013).
32. M. V. Hollegaard, P. Thorsen, B. Norgaard-Pedersen, D. M. Hougaard, Genotyping whole-genome-amplified DNA from 3- to 25-year-old neonatal dried blood spot samples with reference to fresh genomic DNA, *Electrophoresis* 30, 2532-2535 (2009).
33. H. M. Miziorko, Enzymes of the mevalonate pathway of isoprenoid biosynthesisArch. *Biochem. Biophys.* 505, 131-143 (2011).
34. T. Mizuguchi, I. Furuta, Y. Watanabe, K. Tsukamoto, H. Tomita, M. Tsujihata, T. Ohta, T. Kishino, N. Matsumoto, H. Minakami, N. Niikawa, K. I. Yoshiura, LRP5, low-density-lipoprotein-receptor-related protein 5, is a determinant for bone mineral density, *J. Hum. Genet.* 49, 80-86 (2004).
35. B. Redl, Human tear lipocalinBiochim. *Biophys. Acta-Protein Struct. Mol. Enzymol.* 1482, 241-248 (2000).
36. M. Krzystek-Korpacka, D. Diakowska, J. Bania, A. Gamian, Expression stability of common housekeeping genes is differently affected by bowel inflammation and cancer: Implications for finding suitable normalizers for inflammatory bowel disease studies, *Inflamm. Bowel Dis.* 20, 1147-1156 (2014).
37. M. Ghani, C. Sato, E. Rogaeva, Segmental duplications in genome-wide significant loci and housekeeping genes; warning for GAPDH and ACTB, *Neurobiol. Aging* 34 (2013), doi:10.1016/j.neurobiolaging.2012.11.006.
38. D. Tsikas, A proposal for comparing methods of quantitative analysis of endogenous compounds in biological systems by using the relative lower limit of quantification (rLLOQ), *J. Chromatogr. B Anal. Technol. Biomed. Life Sci.* 877, 2244-2251 (2009).
39. W. R. Rodriguez, N. Christodoulides, P. N. Floriano, S. Graham, S. Mohanty, M. Dixon, M. Hsiang, T. Peter, S. Zavahir, I. Thior, D. Romanovicz, B. Bernard, A. P. Goodey, B. D. Walker, J. T. McDevitt, A microchip CD4 counting method for HIV monitoring in resource-poor settings, *PLoS Med.* 2, 0663-0672 (2005).
40. D. M. Moore, R. S. Hogg, B. Yip, K. Craib, E. Wood, J. S. Montaner, CD4 percentage is an independent predictor of survival in patients starting antiretroviral therapy with absolute CD4 cell counts between 200 and 350 cells/microL, *HIV Med* 7, 383-388 (2006).
41. L. M. Yu, P. J. Easterbrook, T. Marshall, Relationship between CD4 count and CD4% in HIV-infected people, *Int. J. Epidemiol.* 26, 1367-1372 (1997).
42. S. J. Read, Recovery efficiencies of nucleic acid extraction kits as measured by quantitative LightCycler™ PCR, *J Clin. Pathol.-Mol. Pathol.* 54, 86-90 (2001).
43. F. Hauck, C. Klein, Pathogenic mechanisms and clinical implications of congenital neutropenia syndromes *Curr. Opin. Allergy Clin. Immunol.* 13, 596-606 (2013).
44. K. Bin Dhuban, C. A. Piccirillo, The immunological and genetic basis of immune dysregulation, polyendocrinopathy, enteropathy, X-linked syndrome *Curr. Opin. Allergy Clin. Immunol.* 15, 525-532 (2015).
45. R. E. Schmidt, B. Grimbacher, T. Witte, Autoimmunity and primary immunodeficiency: Two sides of the same coin?*Nat. Rev. Rheumatol.* 14, 7-18 (2018).
46. L. Brown, J. Xu-Bayford, Z. Allwood, M. Slatter, A. Cant, E. G. Davies, P. Veys, A. R. Gennery, H. B. Gaspar, Neonatal diagnosis of severe combined immunodeficiency leads to significantly improved survival outcome: The case for newborn screening, *Blood* 117, 3243-3246 (2011).
47. S. Borte, U. Von Döbeln, A. Fasth, N. Wang, M. Janzi, J. Winiarski, U. Sack, Q. Pan-Hammarström, M. Borte, L. Hammarström, Neonatal screening for severe primary immunodeficiency diseases using high-throughput triplex real-time PCR, *Blood* 119, 2552-2555 (2012).
48. A. Boldt, S. Borte, S. Fricke, K. Kentouche, F. Emmrich, M. Borte, F. Kahlenberg, U. Sack, Eight-color immunophenotyping of T-, B-, and NK-cell subpopulations for characterization of chronic immunodeficiencies, *Cytom. Part B-Clin. Cytom.* 86, 191-206 (2014).
49. E. E. Holmes, M. Jung, S. Meller, A. Leisse, V. Sailer, J. Zech, M. Mengdehl, L. A. Garbe, B. Uhl, G. Kristiansen, D. Dietrich, Performance evaluation of kits for bisulfite-conversion of DNA from tissues, cell lines, FFPE tissues, aspirates, lavages, effusions, plasma, serum, and urine, *PLoS One* 9 (2014), doi:10.1371/journal.pone.0093933.
50. J. E. Stajich, An Introduction to BioPerl., *Methods Mol. Biol.* 406, 535-548 (2007).

51. M. Barbaro, A. Ohlsson, S. Borte, S. Jonsson, R. H. Zetterström, J. King, J. Winiarski, U. von Döbeln, L. Hammarström, Newborn Screening for Severe Primary Immunodeficiency Diseases in Sweden-a 2-Year Pilot TREC and KREC Screening Study, *J. Clin. Immunol.* 37, 51-60 (2017).

The invention claimed is:

1. A method for producing and detecting a panel of amplicons, the method comprising the steps of
   a) bisulfite treating isolated genomic DNA from a human blood cell sample containing immune cells to convert unmethylated cytosines into uracil;
   b) amplifying the bisulfite treated DNA to produce the panel of amplicons;
   wherein said amplifying comprises amplification and/or qPCR using:
      a thymidine-cytosine (TpG) template carrying targets of converted genomic regions of CD3gamma/delta, CD4, CD8beta, lipoprotein receptor-related protein 5 (LRP5), mevalonate pyrophosphate decarboxylase (MVD), and lipocalin-2 (LCN2), and
      primer pairs and probes for the converted genomic regions of CD3gamma/delta, CD4, CD8beta, LRP5, MVD, and LCN2, the primer pairs and probes selected from SEQ ID NOs: 3 to 12 for CD4, SEQ ID NOs: 13 to 20 for CD8beta, SEQ ID NOs: 21 to 28 for LRP5, SEQ ID NOs: 29 to 36 for MVD, SEQ ID NOs: 37 to 44 for LCN2, and SEQ ID NOs: 45 to 56 for CD3gamma/delta, and
   c) detecting the panel of amplicons.

2. The method according to claim 1, further comprising an analysis of the methylation status of an amplicon for CD3 epsilon.

3. The method according to claim 1, further comprising using a demethylation standard gene selected from a gene expressed in all cells.

4. The method according to claim 3, further comprising using an in silico bisulfite-converted recombinant nucleic acid comprising a sequence inversing all CpG dinucleotides to GpC of said demethylation standard gene (GAP[GC] construct).

5. The method according to claim 1, further comprising using a calibrator plasmid comprising one copy of each amplicon sequence in its unconverted genomic state.

6. The method according to claim 1, wherein said detection of the panel of amplicons further comprises a quantification of CD4+ T cells, CD8+ T cells, B cells, natural killer (NK) cells, and neutrophils.

7. The method according to claim 1, wherein said method further comprises an additional flow cytometry (FCM) of said immune cells.

8. The method according to claim 1, wherein the panel of amplicons comprises amplicons for CD3gamma/delta, CD4, CD8beta, LRP5, MVD, and LCN2.

9. The method according to claim 1, wherein said human blood cell sample is selected from peripheral blood, capillary blood, venous blood, and subfractions thereof.

10. The method of claim 1, wherein the human blood cell sample is taken from a newborn.

11. The method of claim 3, wherein the standard gene is a housekeeping gene.

12. The method of claim 11, wherein the housekeeping gene comprises glyceraldehyde 3-phosphate dehydrogenase (GAPDH) or beta-actin.

13. The method of claim 12, wherein the method uses primers and probes selected from SEQ ID NOs: 57 to 61 for GAPDH.

14. The method of claim 4, wherein the method uses primers and probes selected from SEQ ID NOs: 62 to 64 for the GAP[GC] construct.

15. The method of claim 5, wherein the unconverted genomic state is in an unmethylated state.

16. The method of claim 8, further comprising an analysis of the methylation status of the amplicons for CD3gamma/delta, CD4, CD8beta, LRP5, MVD, and LCN2.

17. The method of claim 9, wherein said human blood cell sample is selected from peripheral blood monocytes, blood clots, and dried blood spots.

* * * * *

```
                        SEQUENCE LISTING

<160> NUMBER OF SEQ ID NOS: 64

<210> SEQ ID NO 1
<211> LENGTH: 22
<212> TYPE: DNA
<213> ORGANISM: Homo sapiens

<400> SEQUENCE: 1
ggtttaggag gggttgtata tt                                              22

<210> SEQ ID NO 2
<211> LENGTH: 22
<212> TYPE: DNA
<213> ORGANISM: Homo sapiens

<400> SEQUENCE: 2
ggtttaggag gggttgtata tt                                              22

<210> SEQ ID NO 3
<211> LENGTH: 21
<212> TYPE: DNA
<213> ORGANISM: Homo sapiens

<400> SEQUENCE: 3
gggttagagt ttagggttgt t                                               21

<210> SEQ ID NO 4
<211> LENGTH: 23
<212> TYPE: DNA
<213> ORGANISM: Homo sapiens

<400> SEQUENCE: 4
actatcccca atatcctcta ctt                                             23

<210> SEQ ID NO 5
<211> LENGTH: 26
<212> TYPE: DNA
<213> ORGANISM: Homo sapiens

<400> SEQUENCE: 5
tctaaaatat acaaaactaa cccaat                                          26

<210> SEQ ID NO 6
<211> LENGTH: 22
<212> TYPE: DNA
<213> ORGANISM: Homo sapiens

<400> SEQUENCE: 6
gtgttagata gagtttgggg gt                                              22

<210> SEQ ID NO 7
<211> LENGTH: 30
<212> TYPE: DNA
<213> ORGANISM: Homo sapiens

<400> SEQUENCE: 7
ccctactctt ataataaaca tttttatcaa                                      30

<210> SEQ ID NO 8
```

```
<211> LENGTH: 27
<212> TYPE: DNA
<213> ORGANISM: Homo sapiens

<400> SEQUENCE: 8
gaaattattt tttgagtgtt tttaatg                                    27

<210> SEQ ID NO 9
<211> LENGTH: 26
<212> TYPE: DNA
<213> ORGANISM: Homo sapiens

<400> SEQUENCE: 9
tgattttgag ggtggtggtt attttg                                     26

<210> SEQ ID NO 10
<211> LENGTH: 28
<212> TYPE: DNA
<213> ORGANISM: Homo sapiens

<400> SEQUENCE: 10
ccctactctt ataataaaca tttttatc                                   28

<210> SEQ ID NO 11
<211> LENGTH: 28
<212> TYPE: DNA
<213> ORGANISM: Homo sapiens

<400> SEQUENCE: 11
ggaaattatt tttcgagtgt ttttaacg                                   28

<210> SEQ ID NO 12
<211> LENGTH: 23
<212> TYPE: DNA
<213> ORGANISM: Homo sapiens

<400> SEQUENCE: 12
attttgaggg cggcggttat ttt                                        23

<210> SEQ ID NO 13
<211> LENGTH: 22
<212> TYPE: DNA
<213> ORGANISM: Homo sapiens

<400> SEQUENCE: 13
aatgttttat ttgggggttt at                                         22

<210> SEQ ID NO 14
<211> LENGTH: 23
<212> TYPE: DNA
<213> ORGANISM: Homo sapiens

<400> SEQUENCE: 14
cctactactc cttcaattct caa                                        23

<210> SEQ ID NO 15
<211> LENGTH: 30
<212> TYPE: DNA
<213> ORGANISM: Homo sapiens

<400> SEQUENCE: 15
gtggttaaga aattaatagg aaaaagaatg                                 30
```

```
<210> SEQ ID NO 16
<211> LENGTH: 21
<212> TYPE: DNA
<213> ORGANISM: Homo sapiens

<400> SEQUENCE: 16
cttccccacc acaatacaac a                                          21

<210> SEQ ID NO 17
<211> LENGTH: 31
<212> TYPE: DNA
<213> ORGANISM: Homo sapiens

<400> SEQUENCE: 17
tgtttgtgag gtatttagtt gatgggagtt t                               31

<210> SEQ ID NO 18
<211> LENGTH: 27
<212> TYPE: DNA
<213> ORGANISM: Homo sapiens

<400> SEQUENCE: 18
ggttaagaaa ttaataggaa aaagaac                                    27

<210> SEQ ID NO 19
<211> LENGTH: 18
<212> TYPE: DNA
<213> ORGANISM: Homo sapiens

<400> SEQUENCE: 19
ccccatatta cttccccg                                              18

<210> SEQ ID NO 20
<211> LENGTH: 28
<212> TYPE: DNA
<213> ORGANISM: Homo sapiens

<400> SEQUENCE: 20
cgtttgtgag gtatttagtc gacgggag                                   28

<210> SEQ ID NO 21
<211> LENGTH: 22
<212> TYPE: DNA
<213> ORGANISM: Homo sapiens

<400> SEQUENCE: 21
atttttgtgt gattttaggg tt                                         22

<210> SEQ ID NO 22
<211> LENGTH: 22
<212> TYPE: DNA
<213> ORGANISM: Homo sapiens

<400> SEQUENCE: 22
atatccaaat atcctaccct cc                                         22

<210> SEQ ID NO 23
<211> LENGTH: 25
<212> TYPE: DNA
<213> ORGANISM: Homo sapiens

<400> SEQUENCE: 23
aatattacaa ccatacaccc aacaa                                      25
```

<210> SEQ ID NO 24
<211> LENGTH: 29
<212> TYPE: DNA
<213> ORGANISM: Homo sapiens

<400> SEQUENCE: 24
aagtgataga attttatgtt tttttatg                               29

<210> SEQ ID NO 25
<211> LENGTH: 27
<212> TYPE: DNA
<213> ORGANISM: Homo sapiens

<400> SEQUENCE: 25
ttagttgagg tgaggtgttt tgttagt                                27

<210> SEQ ID NO 26
<211> LENGTH: 21
<212> TYPE: DNA
<213> ORGANISM: Homo sapiens

<400> SEQUENCE: 26
attaatatta cgaccgtacg c                                      21

<210> SEQ ID NO 27
<211> LENGTH: 25
<212> TYPE: DNA
<213> ORGANISM: Homo sapiens

<400> SEQUENCE: 27
cgatagaatt ttacgttttt tttac                                  25

<210> SEQ ID NO 28
<211> LENGTH: 19
<212> TYPE: DNA
<213> ORGANISM: Homo sapiens

<400> SEQUENCE: 28
acgaaacgcc tcgcctcga                                         19

<210> SEQ ID NO 29
<211> LENGTH: 22
<212> TYPE: DNA
<213> ORGANISM: Homo sapiens

<400> SEQUENCE: 29 aaccccctaat ttccttctta ct                                    22

<210> SEQ ID NO 30
<211> LENGTH: 21
<212> TYPE: DNA
<213> ORGANISM: Homo sapiens

<400> SEQUENCE: 30
ggtgtgggtt tgagtttatt t                                      21

<210> SEQ ID NO 31
<211> LENGTH: 27
<212> TYPE: DNA
<213> ORGANISM: Homo sapiens

<400> SEQUENCE: 31
ggttttgtgg tattttata gagtagt                                 27

<210> SEQ ID NO 32
<211> LENGTH: 19
<212> TYPE: DNA
<213> ORGANISM: Homo sapiens

<400> SEQUENCE: 32
ccatatacac cctcctcaa                                              19

<210> SEQ ID NO 33
<211> LENGTH: 25
<212> TYPE: DNA
<213> ORGANISM: Homo sapiens

<400> SEQUENCE: 33
ccctaaacca cctcttcccc tacac                                       25

<210> SEQ ID NO 34
<211> LENGTH: 25
<212> TYPE: DNA
<213> ORGANISM: Homo sapiens

<400> SEQUENCE: 34
ttttgtggta tttttataga gtagc                                       25

<210> SEQ ID NO 35
<211> LENGTH: 18
<212> TYPE: DNA
<213> ORGANISM: Homo sapiens

<400> SEQUENCE: 35
ccatatacgc cctcctcg                                               18

<210> SEQ ID NO 36
<211> LENGTH: 20
<212> TYPE: DNA
<213> ORGANISM: Homo sapiens

<400> SEQUENCE: 36
aaaccgcctc ttcccctacg                                             20

<210> SEQ ID NO 37
<211> LENGTH: 21
<212> TYPE: DNA
<213> ORGANISM: Homo sapiens

<400> SEQUENCE: 37
gattaggttt gaggtggagt t                                           21

<210> SEQ ID NO 38
<211> LENGTH: 22
<212> TYPE: DNA
<213> ORGANISM: Homo sapiens

<400> SEQUENCE: 38
tatccctacc aaaaatacaa ca                                          22

<210> SEQ ID NO 39
<211> LENGTH: 21
<212> TYPE: DNA
<213> ORGANISM: Homo sapiens

<400> SEQUENCE: 39
accaaaaata caacacttca a                                                   21

<210> SEQ ID NO 40
<211> LENGTH: 23
<212> TYPE: DNA
<213> ORGANISM: Homo sapiens

<400> SEQUENCE: 40
ggtaattgtt agtaattttt gtg                                                 23

<210> SEQ ID NO 41
<211> LENGTH: 21
<212> TYPE: DNA
<213> ORGANISM: Homo sapiens

<400> SEQUENCE: 41
cactctcccc atccctctat c                                                   21

<210> SEQ ID NO 42
<211> LENGTH: 21
<212> TYPE: DNA
<213> ORGANISM: Homo sapiens

<400> SEQUENCE: 42
taccaaaaat acaacactcc g                                                   21

<210> SEQ ID NO 43
<211> LENGTH: 24
<212> TYPE: DNA
<213> ORGANISM: Homo sapiens

<400> SEQUENCE: 43
aggtaattgt tagtaatttt tacg                                                24

<210> SEQ ID NO 44
<211> LENGTH: 23
<212> TYPE: DNA
<213> ORGANISM: Homo sapiens

<400> SEQUENCE: 44
ctcactctcc ccgtccctct atc                                                 23

<210> SEQ ID NO 45
<211> LENGTH: 21
<212> TYPE: DNA
<213> ORGANISM: Homo sapiens

<400> SEQUENCE: 45 gattttaga tgtttggggt t                                                    21

<210> SEQ ID NO 46
<211> LENGTH: 22
<212> TYPE: DNA
<213> ORGANISM: Homo sapiens

<400> SEQUENCE: 46
ttattccacc tattaccttc ca                                                  22

<210> SEQ ID NO 47
<211> LENGTH: 22
<212> TYPE: DNA
<213> ORGANISM: Homo sapiens

<400> SEQUENCE: 47
tttaggttgt gtgtaaatgt gg                                                   22

<210> SEQ ID NO 48
<211> LENGTH: 22
<212> TYPE: DNA
<213> ORGANISM: Homo sapiens

<400> SEQUENCE: 48
ataaacctca ctcccatcaa ta                                                   22

<210> SEQ ID NO 49
<211> LENGTH: 23
<212> TYPE: DNA
<213> ORGANISM: Homo sapiens

<400> SEQUENCE: 49
aggatgagga tagttaggtt ttt                                                  23

<210> SEQ ID NO 50
<211> LENGTH: 22
<212> TYPE: DNA
<213> ORGANISM: Homo sapiens

<400> SEQUENCE: 50
aatccctcct aaattcatta cc                                                   22

<210> SEQ ID NO 51
<211> LENGTH: 22
<212> TYPE: DNA
<213> ORGANISM: Homo sapiens

<400> SEQUENCE: 51
cctaaacact accacatctc aa                                                   22

<210> SEQ ID NO 52
<211> LENGTH: 24
<212> TYPE: DNA
<213> ORGANISM: Homo sapiens

<400> SEQUENCE: 52
agaaatttag ttgttatggt ttgt                                                 24

<210> SEQ ID NO 53
<211> LENGTH: 27
<212> TYPE: DNA
<213> ORGANISM: Homo sapiens

<400> SEQUENCE: 53
aaaaaaccat caaccccata acacaaa                                              27

<210> SEQ ID NO 54
<211> LENGTH: 21
<212> TYPE: DNA
<213> ORGANISM: Homo sapiens

<400> SEQUENCE: 54
ctaaacacta ccacatctcg a                                                    21

<210> SEQ ID NO 55
<211> LENGTH: 22
<212> TYPE: DNA
<213> ORGANISM: Homo sapiens

```
<400> SEQUENCE: 55
aaatttagtt gttacggttt gc                                              22

<210> SEQ ID NO 56
<211> LENGTH: 18
<212> TYPE: DNA
<213> ORGANISM: Homo sapiens

<400> SEQUENCE: 56
ccgtcgaccc cataacgc                                                   18

<210> SEQ ID NO 57
<211> LENGTH: 22
<212> TYPE: DNA
<213> ORGANISM: Homo sapiens

<400> SEQUENCE: 57
aaacccactt ctttaattta cc                                              22

<210> SEQ ID NO 58
<211> LENGTH: 17
<212> TYPE: DNA
<213> ORGANISM: Homo sapiens

<400> SEQUENCE: 58
tgggggtagg gtagttg                                                    17

<210> SEQ ID NO 59
<211> LENGTH: 22
<212> TYPE: DNA
<213> ORGANISM: Homo sapiens

<400> SEQUENCE: 59 ggttttggt attgtaggtt tt                                               22

<210> SEQ ID NO 60
<211> LENGTH: 21
<212> TYPE: DNA
<213> ORGANISM: Homo sapiens

<400> SEQUENCE: 60
ccaattacaa cataacaacc a                                               21

<210> SEQ ID NO 61
<211> LENGTH: 29
<212> TYPE: DNA
<213> ORGANISM: Homo sapiens

<400> SEQUENCE: 61
tgtttggatg ttgtgtttgt ggtagagtg                                       29

<210> SEQ ID NO 62
<211> LENGTH: 22
<212> TYPE: DNA
<213> ORGANISM: Homo sapiens

<400> SEQUENCE: 62
ggttttgtgt atgttaggtt tg                                              22

<210> SEQ ID NO 63
<211> LENGTH: 22
<212> TYPE: DNA
<213> ORGANISM: Homo sapiens
```

```
<400> SEQUENCE: 63
ccacattaca acataaacac ac                                            22

<210> SEQ ID NO 64
<211> LENGTH: 29
<212> TYPE: DNA
<213> ORGANISM: Homo sapiens

<400> SEQUENCE: 64
tgttgtgatg ttggttttgg tgtagaggt                                     29
```